United States Patent
Nozoe et al.

(10) Patent No.: US 9,676,956 B2
(45) Date of Patent: Jun. 13, 2017

(54) (METH)ACRYLIC RESIN COMPOSITION, FILM, POLARIZING PLATE PROTECTIVE FILM, POLARIZING PLATE, AND LIQUID CRYSTAL DISPLAY DEVICE

(71) Applicant: FUJIFILM Corporation, Tokyo (JP)

(72) Inventors: Yutaka Nozoe, Kanagawa (JP); Shusuke Arita, Kanagawa (JP); Hajime Nakayama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/262,791

(22) Filed: Sep. 12, 2016

(65) Prior Publication Data

US 2016/0376463 A1 Dec. 29, 2016

Related U.S. Application Data

(63) Continuation of application No. PCT/JP2015/059268, filed on Mar. 25, 2015.

(30) Foreign Application Priority Data

Mar. 28, 2014 (JP) .................................. 2014-070533

(51) Int. Cl.
*G02B 5/30* (2006.01)
*C08L 33/12* (2006.01)
(Continued)

(52) U.S. Cl.
CPC ............ *C09D 133/10* (2013.01); *C07C 39/17* (2013.01); *C07C 39/42* (2013.01); *C08F 220/14* (2013.01);
(Continued)

(58) Field of Classification Search
CPC .................................. C08L 33/12; C08K 5/13
(Continued)

(56) References Cited

FOREIGN PATENT DOCUMENTS

| JP | 4410540 B2 | 11/2009 |
|---|---|---|
| JP | 2011021083 A | * 2/2011 |
| JP | 2011-144344 A | 7/2011 |

* cited by examiner

*Primary Examiner* — Vu A Nguyen
(74) *Attorney, Agent, or Firm* — Edwards Neils LLC; Jean C. Edwards, Esq.

(57) ABSTRACT

There is provided a (meth)acrylic resin composition, containing a (meth)acrylic resin; a compound denoted by General Formula (1) described below; and a specific compound:

General Formula (1)

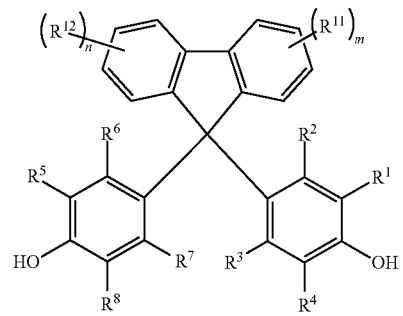

wherein $R^1$ to $R^8$ each independently represent a hydrogen atom, a halogen atom, a hydroxyl group, or a hydrocarbon group having 1 to 6 carbon atoms, $R^{11}$ and $R^{12}$ each independently represent a hydrogen atom, a halogen atom, or a hydrocarbon group having 1 to 12 carbon atoms, m and n each independently represent an integer of 0 to 4, in a case where m and n represent an integer of greater than or equal to 2, a plurality of $R^{11}$'s and $R^{12}$'s may be identical to each (Continued)

other or different from each other, at least two $R^{11}$'s, at least two $R^{12}$'s, or $R^{11}$ and $R^{12}$ may form a ring by being linked to each other.

12 Claims, 1 Drawing Sheet

(51) Int. Cl.
　　*C08K 5/13*　　　　(2006.01)
　　*C09D 133/10*　　(2006.01)
　　*G02B 1/14*　　　　(2015.01)
　　*C08F 220/14*　　(2006.01)
　　*G02F 1/1335*　　(2006.01)
　　*C08K 5/00*　　　　(2006.01)
　　*C07C 39/17*　　　(2006.01)
　　*C07C 39/42*　　　(2006.01)
　　*C09D 7/12*　　　　(2006.01)
　　*C08K 5/053*　　　(2006.01)

(52) U.S. Cl.
　　CPC .............. *C08K 5/0025* (2013.01); *C08K 5/13* (2013.01); *C09D 7/1233* (2013.01); *G02B 1/14* (2015.01); *G02B 5/305* (2013.01); *G02B 5/3033* (2013.01); *G02F 1/133528* (2013.01); *C07C 2103/12* (2013.01); *C07C 2103/18* (2013.01); *C08K 5/053* (2013.01); *G02F 2201/50* (2013.01)

(58) Field of Classification Search
　　USPC ........................................................ 524/556
　　See application file for complete search history.

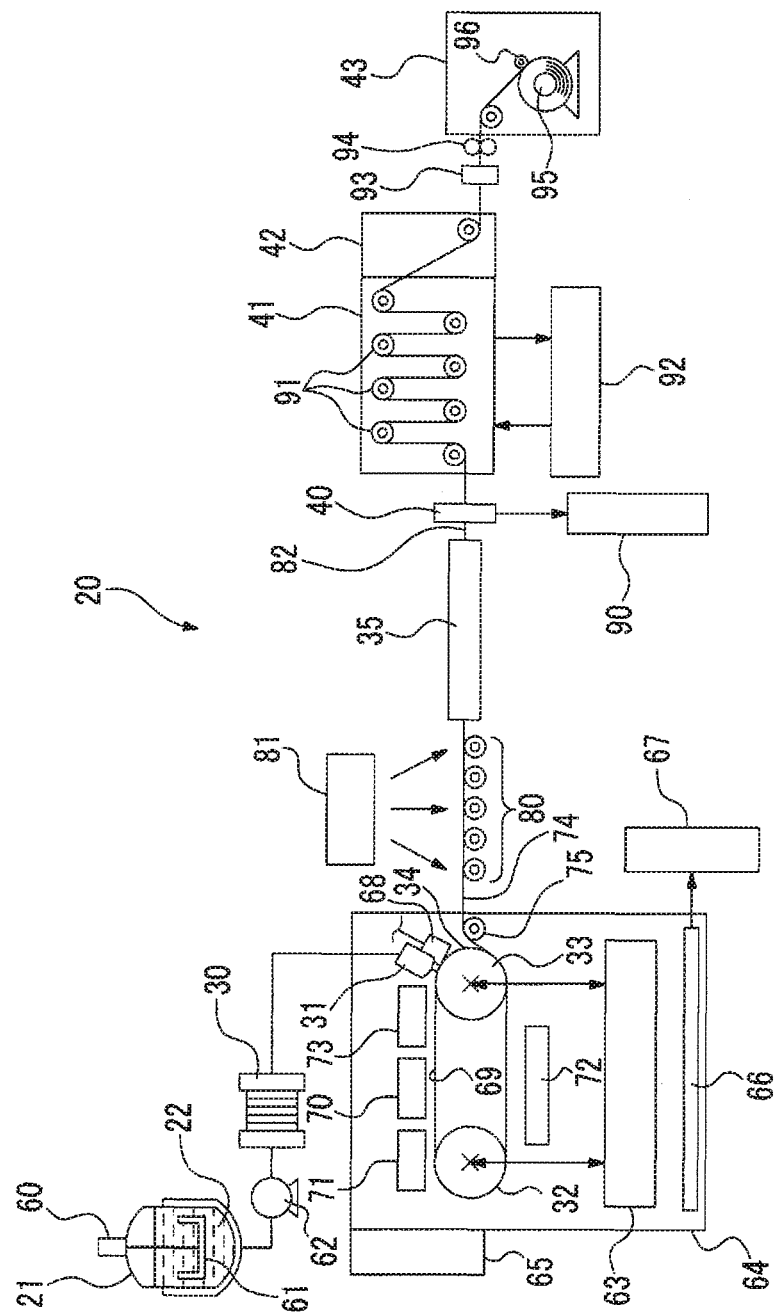

(METH)ACRYLIC RESIN COMPOSITION, FILM, POLARIZING PLATE PROTECTIVE FILM, POLARIZING PLATE, AND LIQUID CRYSTAL DISPLAY DEVICE

CROSS REFERENCE TO RELATED APPLICATION

This is a continuation of International Application No. PCT/JP2015/059268 filed on Mar. 25, 2015, which was published under Article 21(2) in Japanese, and claims priority from Japanese Patent Application No. 2014-70533 filed on Mar. 28, 2014, the entire disclosures of which are incorporated herein by reference in their entirety.

BACKGROUND OF THE INVENTION

1. Field of the Invention

The present invention relates to a (meth)acrylic resin composition, a film, a polarizing plate protective film, a polarizing plate, and a liquid crystal display device.

2. Description of the Related Art

A demand for using a liquid crystal display device as a liquid crystal display or the like of a liquid crystal television or a personal computer has increased. In general, a liquid crystal display device is configured of a liquid crystal cell in which a transparent electrode, a liquid crystal layer, a color filter, and the like are interposed between glass plates, and two polarizing plates disposed on both sides thereof, and the polarizing plate has a configuration including a polarizer and at least one polarizing plate protective film.

On the other hand, the size of the liquid crystal display device has been rapidly enlarged, and the application of the liquid crystal display device has been diversified according to advancements in the recent technology, and the liquid crystal display device is assumed to be used in various environments. For example, in a case where the liquid crystal display device is used outside, deterioration due to moisture absorption of the polarizer becomes a problem, and a film which is used as the polarizing plate protective film has been required to have properties such as low moisture permeability. A film formed of a (meth)acrylic resin such as polymethyl methacrylate (PMMA) (a (meth)acrylic resin film) has been known as a film having low moisture permeability.

On the other hand, in JP4410540B and JP2011-144344A, it is disclosed that 9,9-bis(mono to trihydroxy phenyl) fluorenes are added to cellulose acylate or polycarbonate, and thus, the refractive index of a resin composition increases, or a resin is plasticized.

SUMMARY OF THE INVENTION

When the (meth)acrylic resin film is used as a polarizing plate protective film, the (meth)acrylic resin film is further required to have low moisture permeability. However, according to the study of the present inventors, it has been found that in a case where an additive is mixed with an (meth)acrylic resin in order to have low moisture permeability, the (meth)acrylic resin is plasticized according to the additive, and thus, a glass transition temperature (Tg) may decrease, or haze may increase. Further, it has been found that the (meth)acrylic resin itself has properties of being hardly colored, but the additive is colored.

An object of the present invention is to provide a (meth) acrylic resin composition from which a film having high Tg, excellent heat resistance, low haze, reduced coloration, and low moisture permeability is able to be manufactured. In addition, another object of the present invention is to provide a film formed by using the (meth)acrylic resin composition, and a polarizing plate and a liquid crystal display device including the film.

As a result of intensive studies of the present inventors, it has been found that the objects described above are attained by using a specific compound having a fluorene structure, and a compound preventing the compound from being oxidized. It is considered that the specific compound having a fluorene structure has a rigid skeleton, and thus, Tg does not decrease even in a case where the specific compound is added to the (meth)acrylic resin, and the specific compound exists to fill a gap between molecular chains of the (meth) acrylic resin, and thus, it is possible to decrease the moisture permeability of the film.

That is, the present invention is as follows.

[1] A (meth)acrylic resin composition, containing: a (meth)acrylic resin; a compound denoted by General Formula (1) described below; and a compound preventing the compound denoted by General Formula (1) described below from being oxidized.

General Formula (1)

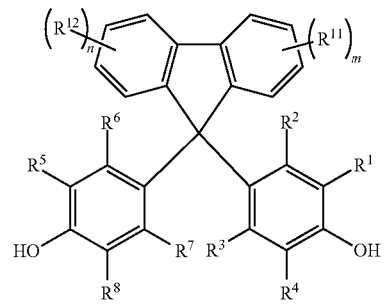

$R^1$ to $R^8$ each independently represent a hydrogen atom, a halogen atom, a hydroxyl group, or a hydrocarbon group having 1 to 6 carbon atoms. $R^{11}$ and $R^{12}$ each independently represent a hydrogen atom, a halogen atom, or a hydrocarbon group having 1 to 12 carbon atoms. m and n each independently represent an integer of 0 to 4. In a case where m and n represent an integer of greater than or equal to 2, a plurality of $R^{11}$'s and $R^{12}$'s may be identical to each other or different from each other. At least two $R^{11}$'s, at least two $R^{12}$'s, or $R^{11}$ and $R^{12}$ may form a ring by being linked to each other.

[2] The (meth)acrylic resin composition according to [1], in which in General Formula (1), $R^2$, $R^3$, $R^4$, $R^6$, $R^7$, and $R^8$ represent a hydrogen atom.

[3] The (meth)acrylic resin composition according to [1] or [2], in which in General Formula (1) described above, $R^1$ and $R^5$ each independently represent a hydrogen atom or a methyl group.

[4] The (meth)acrylic resin composition according to any one of [1] to [3], in which in General Formula (1) described above, m and n represent 0.

[5] The (meth)acrylic resin composition according to any one of [1] to [4], in which the compound preventing the compound denoted by General Formula (1) described above from being oxidized is a phenol-based antioxidant, a sulfur-based antioxidant, or an amide-based antioxidant.

[6] The (meth)acrylic resin composition according to any one of [1] to [5], in which a weight-average molecular weight of the (meth)acrylic resin is 80,000 to 2,500,000.

[7] The (meth)acrylic resin composition according to any one of [1] to [6], in which the weight-average molecular weight of the (meth)acrylic resin is 250,000 to 2,000,000.

[8] The (meth)acrylic resin composition according to any one of [1] to [7], in which the (meth)acrylic resin is a (meth)acrylic resin in which a content ratio of a structural unit derived from methyl methacrylate is greater than or equal to 95 mass %, and a content ratio of a structural unit derived from alkyl (meth)acrylate other than the methyl methacrylate is less than 5 mass %.

[9] A film obtained by performing film formation with respect to the (meth)acrylic resin composition according to any one of [1] to [8].

[10] A polarizing plate protective film, comprising: the film according to [9].

[11] A polarizing plate, comprising: the polarizing plate protective film according to [10].

[12] A liquid crystal display device, comprising the polarizing plate according to [11].

According to the present invention, it is possible to provide a (meth)acrylic resin composition from which a film having high Tg, excellent heat resistance, low haze, reduced coloration, and low moisture permeability is able to be manufactured. In addition, according to the present invention, it is possible to provide a film formed by using the (meth)acrylic resin composition, and a polarizing plate and a liquid crystal display device including the film.

BRIEF DESCRIPTION OF THE DRAWINGS

The FIGURE is a schematic view illustrating a manufacturing step of a (meth)acrylic resin film.

DESCRIPTION OF THE PREFERRED EMBODIMENTS

Hereinafter, the present invention will be described in detail. The description of configuration requirements described below is based on representative embodiments or specific examples, but the present invention is not limited to the embodiments. Further, herein, a numerical range denoted by using "to" indicates a range including numerical values before and after "to" as the lower limit value and the upper limit value. In addition, (meth)acryl indicates methacryl or acryl.

<(Meth)Acrylic Resin Composition>

A (meth)acrylic resin composition of the present invention is a (meth)acrylic resin composition containing a (meth)acrylic resin, a compound denoted by General Formula (1) described below, and a compound preventing the compound denoted by General Formula (1) described below from being oxidized.

General Formula (1)

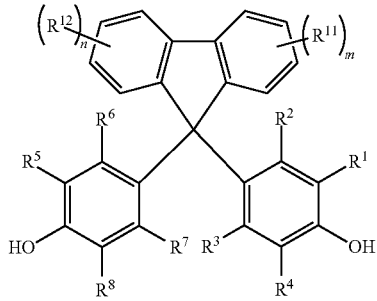

$R^1$ to $R^8$ each independently represent a hydrogen atom, a halogen atom, a hydroxyl group, or a hydrocarbon group having 1 to 6 carbon atoms. $R^{11}$ and $R^{12}$ each independently represent a hydrogen atom, a halogen atom, or a hydrocarbon group having 1 to 12 carbon atoms. m and n each independently represent an integer of 0 to 4. In a case where m and n represent an integer of greater than or equal to 2, a plurality of $R^{11}$'s and $R^{12}$'s may be identical to each other or different from each other. At least two $R^{11}$'s, at least two $R^{12}$'s, or $R^{11}$ and $R^{12}$ may form a ring by being linked to each other.

[(Meth)Acrylic Resin]

The "(meth)acrylic resin" of the present invention may be either an "acrylic resin" or a "methacrylic resin", may be a copolymer of the "acrylic resin" and the "methacrylic resin", or may have other structural units as described below.

A (meth)acrylic resin having a structural unit derived from methyl methacrylate is preferable as the (meth)acrylic resin, and the (meth)acrylic resin may or may not have a structural unit derived from alkyl (meth)acrylate other than the methyl methacrylate.

It is preferable that the (meth)acrylic resin is a (meth)acrylic resin in which the content ratio of the structural unit derived from the methyl methacrylate is greater than or equal to 95 mass %, and the content ratio of the structural unit derived from the alkyl (meth)acrylate other than the methyl methacrylate is less than 5 mass %.

In a case where the (meth)acrylic resin has the structural unit derived from the alkyl (meth)acrylate other than the methyl methacrylate, example of the structural unit derived from the alkyl (meth)acrylate are able to include the followings.

(Structural Unit Derived from Alkyl (Meth)Acrylate Other than Methyl Methacrylate)

Examples of the alkyl (meth)acrylate other than the methyl methacrylate include acrylic acid ester such as methyl acrylate, ethyl acrylate, n-butyl acrylate, isobutyl acrylate, t-butyl acrylate, cyclohexyl acrylate, and benzyl acrylate (preferably, alkyl acrylate in which the number of carbon atoms of an alkyl group is 1 to 18); methacrylic acid ester such as ethyl methacrylate, propyl methacrylate, n-butyl methacrylate, isobutyl methacrylate, t-butyl methacrylate, cyclohexyl methacrylate, and benzyl methacrylate (preferably alkyl methacrylate in which the number of carbon atoms of an alkyl group is 2 to 18); and the like, and only one type of the alkyl (meth)acrylate may be used, or two or more types thereof may be used in combination.

(Other Structural Units)

The (meth)acrylic resin which is used in the present invention may also have a structural unit other than the structural units described above. Examples of such a structural unit include an α,β-unsaturated acid such as an acrylic acid and a methacrylic acid, an unsaturated group-containing divalent carboxylic acid such as a maleic acid, a fumaric acid, and an itaconic acid, an aromatic vinyl compound such as styrene and α-methyl styrene, α,β-unsaturated nitrile such as acrylonitrile and methacrylonitrile, maleic anhydride, maleimide, N-substituted maleimide, glutaric anhydride, and the like. Only one type of the structural unit may be independently introduced into the (meth)acrylic resin, or two or more types thereof may be introduced into the (meth)acrylic resin in combination.

Among them, from the viewpoint of thermal decomposition resistance or fluidity of a copolymer, methyl acrylate, ethyl acrylate, n-propyl acrylate, n-butyl acrylate, s-butyl acrylate, 2-ethyl hexyl acrylate, and the like are preferable, and the methyl acrylate or the n-butyl acrylate is particularly preferably used.

(Content Ratio of Structural Unit Derived from Methyl Methacrylate)

In the (meth)acrylic resin, the content ratio of the structural unit derived from the methyl methacrylate is preferably 95 mass % to 100 mass %, is more preferably 97 mass % to 100 mass %, and is even more preferably 100 mass %, from the viewpoint of sufficiently exhibiting the effect of the present invention.

By setting the ratio of the structural unit derived from the methyl methacrylate to be greater than or equal to 95 mass %, a (meth)acrylic resin having high heat resistance is able to be obtained.

In addition, in the (meth)acrylic resin, the content ratio of the structural unit derived from the alkyl (meth)acrylate other than the methyl methacrylate is preferably less than 5 mass %, is more preferably less than 3 mass %, and is particularly preferably 0 mass % (that is, the (meth)acrylic resin does not have the structural unit derived from the alkyl (meth)acrylate other than the methyl methacrylate).

(Manufacturing Method of (Meth)Acrylic Resin)

The (meth)acrylic resin which is able to be used in the (meth)acrylic resin composition of the present invention is available by a commercially available product or a known synthesis method.

Emulsion polymerization, solution polymerization, bulk polymerization, and suspension polymerization are able to be applied as a manufacturing method of the (meth)acrylic resin which is able to be used in the (meth)acrylic resin composition of the present invention. Among them, the emulsion polymerization and the suspension polymerization are more preferable from the viewpoint of manufacturing a polymer of the present invention.

An initiator which is used in general suspension polymerization is able to be used as an initiator of the suspension polymerization, and examples of the initiator include an organic peroxide and an azo compound.

A known suspension stabilizer which is generally used is also able to be used as a suspension stabilizer, and examples of the suspension stabilizer are able to include an organic colloidal polymer substance, an inorganic colloidal polymer substance, inorganic fine particles, and a combination of the substances and a surfactant.

(Weight-Average Molecular Weight of (Meth)Acrylic Resin)

In the present invention, the "weight-average molecular weight" is weight-average molecular weight which is measured by a gel permeation chromatography.

The weight-average molecular weight of the (meth)acrylic resin is not particularly limited, but in order to sufficiently exhibit the effect of the present invention, the weight-average molecular weight of the (meth)acrylic resin is preferably 80,000 to 3,000,000, is more preferably 80,000 to 2,500,000, and is even more preferably 250,000 to 2,000,000. In the (meth)acrylic resin having a weight-average molecular weight in such a range, the weight-average molecular weight is higher than the weight-average molecular weight of a (meth)acrylic resin used in melting film formation, and the (meth)acrylic resin is suitable for solution film formation.

In a case where the weight-average molecular weight of the (meth)acrylic resin is greater than or equal to 80,000, it is possible to increase the viscosity of the (meth)acrylic resin composition, and it is possible to suppress the occurrence of a streak on a casting film at the time of ejecting the (meth)acrylic resin composition from a casting die, even in a case where the concentration of the (meth)acrylic resin in the (meth)acrylic resin composition is low (for example, 10 mass %). In addition, in a case where a weight-average molecular weight Mw of the (meth)acrylic resin is greater than or equal to 80,000, the breaking elongation of a (meth)acrylic resin film at the time of being un-stretched increases, and the handling aptitude at the time of manufacturing the film is excellent.

It is preferable that the weight-average molecular weight of the (meth)acrylic resin is less than or equal to 3,000,000 from the viewpoint of a polymerization process.

In the present invention, the "weight-average molecular weight (Mw)" is a weight-average molecular weight which is measured by a gel permeation chromatography in the following conditions.

Solvent Tetrahydrofuran
Device Name TOSOH HLC-8220GPC
Column Using Three TOSOH TSK Gel Super HZM-H (4.6 mm×15 cm) in Connection.
Column Temperature 25° C.
Sample Concentration 0.1 mass %
Flow Rate 0.35 ml/min
Calibration Curve TSK Standard Polystyrene Manufactured by Tosoh Corporation, Using Calibration Curve of Seven Samples Having Mw of 2,800,000 to 1,050.

(Tg of (Meth)Acrylic Resin)

In the present invention, it is preferable that Tg of the (meth)acrylic resin is higher than or equal to 110° C. from the viewpoint of manufacturing aptitude and heat resistance. The glass transition temperature of the (meth)acrylic resin is preferably 110° C. to 200° C., is more preferably 115° C. to 150° C.

Herein, the glass transition temperature Tg is obtained by using a dynamic viscoelasticity measure device described below. A film sample of the present invention (un-stretched) having a size of 5 mm×30 mm is subjected to humidity adjustment at a temperature of 25° C. and relative humidity of 60% for 2 hours, and then, is measured at a distance between chucks of 20 mm, a temperature rising rate of 2° C./minute, a measurement temperature range of 30° C. to 250° C., and a frequency of 1 Hz by a dynamic viscoelasticity measure device (VIBRON: DVA-225 (manufactured by IT KEISOKU SEIGYO KK)), and when a storage elastic modulus is set as a logarithmic axis on a vertical axis and a temperature (° C.) is set as a linear axis on a horizontal axis, in a rapid decrease in the storage elastic modulus which is observed at the time of the transition of the storage elastic modulus from a solid region to a glass transition region, an intersection of a straight line 1 taken from the solid region and a straight line 2 taken from the glass transition region is a temperature at which the storage elastic modulus rapidly decreases and the film stars to be softened at the time of temperature rising, and is a temperature at which the transition to the glass transition region starts, and thus, is set to the glass transition temperature Tg (dynamic viscoelasticity).

(Concentration of (Meth)Acrylic Resin)

The concentration of the (meth)acrylic resin in the (meth)acrylic resin composition is different according to the thickness of a film to be formed, but is preferably 10 mass % to 40 mass %, is more preferably 10 mass % to 30 mass %, and is even more preferably 15 mass % to 25 mass %. Accordingly, it is possible to obtain a dope composition having suitable viscosity, and it is possible to obtain a film having an excellent surface shape and a desirable thickness.

[Other Resins]

The (meth)acrylic resin composition of the present invention may contain a resin other than the (meth)acrylic resin described above in a range not impairing the effect of the present invention.

Examples of such a resin are able to include an olefin-based thermoplastic resin such as polyethylene, polypropylene, ethylene-propylene copolymer, and poly(4-methyl-1-pentene); a halogen-containing thermoplastic resin such as vinyl chloride and a chlorinated vinyl resin; an acrylic thermoplastic resin such as polymethyl methacrylate; a styrene-based thermoplastic resin such as polystyrene, a methyl styrene-methacrylate copolymer, a styrene-acrylonitrile copolymer, and an acrylonitrile-butadiene-styrene block copolymer; polyester such as polyethylene terephthalate, polybutylene terephthalate, and polyethylene naphthalate; polyamide such as nylon 6, nylon 66, and nylon 610; polyacetal; polycarbonate; polyphenylene oxide; polyphenylene sulfide; polyether ether ketone; polysulfone; polyether sulfone; polyoxy benzylene; polyamide imide; a rubber polymer such as polybutadiene-based rubber and an ABS resin or an ASA resin in which acrylic rubber is formulated, and the like. In the present invention, a cellulose resin such as cellulose acylate is not included as the resin other than the (meth)acrylic resin.

In a case where the resin other than the (meth)acrylic resin is added to the (meth)acrylic resin composition, the resin to be added may be in a compatible state, or may be mixed without being dissolved.

[Compound Denoted by General Formula (1)]

The (meth)acrylic resin composition of the present invention contains a compound denoted by General Formula (1) described below.

General Formula (1)

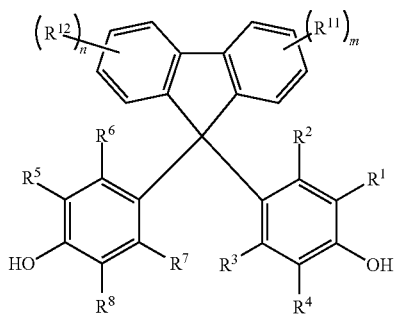

$R^1$ to $R^8$ each independently represent a hydrogen atom, a halogen atom, a hydroxyl group, or a hydrocarbon group having 1 to 6 carbon atoms. $R^{11}$ and $R^{12}$ each independently represent a hydrogen atom, a halogen atom, or a hydrocarbon group having 1 to 12 carbon atoms. m and n each independently represent an integer of 0 to 4. In a case where m and n represent an integer of greater than or equal to 2, a plurality of R's and $R^{12}$'s may be identical to each other or different from each other. At least two $R^{11}$'s, at least two $R^{12}$'s, or $R^{11}$ and $R^{12}$ may form a ring by being linked to each other.

In General Formula (1), $R^1$ to $R^8$ each independently represent a hydrogen atom, a halogen atom, a hydroxyl group, or a hydrocarbon group having 1 to 6 carbon atoms. A fluorine atom, a chlorine atom, a bromine atom, or an iodine atom is preferable as the halogen atom, and the chlorine atom is more preferable. Examples of the hydrocarbon group having 1 to 6 carbon atoms include an alkyl group, an alkenyl group, an alkynyl group, and an aryl group. Examples of the alkyl group having 1 to 6 carbon atoms include a straight chain alkyl group, a branch alkyl group, or a cyclic alkyl group, and specifically, a methyl group, an ethyl group, an isopropyl group, a t-butyl group, and a cyclohexyl group are preferable.

It is preferable that $R^2$, $R^3$, $R^4$, $R^6$, $R^7$, and $R^8$ represent a hydrogen atom from the viewpoint of compatibility and moisture permeability.

It is preferable that $R^1$ and $R^5$ each independently represent a hydrogen atom or a methyl group from the viewpoint of moisture permeability.

$R^{11}$ and $R^{12}$ each independently represent a hydrogen atom, a halogen atom, or a hydrocarbon group having 1 to 12 carbon atoms. A fluorine atom, a chlorine atom, a bromine atom, or an iodine atom is preferable as the halogen atom, and the chlorine atom is more preferable. Examples of the hydrocarbon group having 1 to 12 carbon atoms include an alkyl group, an alkenyl group, an alkynyl group, and an aryl group. Examples of the alkyl group include a straight chain alkyl group, a branch alkyl group, or a cyclic alkyl group.

In a case where m and n represent an integer of greater than or equal to 2, a plurality of $R^{11}$'s and $R^{12}$'s may be identical to each other or different from each other. At least two $R^{11}$'s, at least two $R^{12}$'s, or $R^{11}$ and $R^{12}$ may form a ring by being linked to each other. A ring to be formed may be an aliphatic ring or an aromatic ring, and the aromatic ring is preferable, and a benzene ring is more preferable.

m and n each independently represent an integer of 0 to 4, preferably represent an integer of 0 to 2, more preferably represent 0 or 1, and particularly preferably represent 0.

A specific example of the compound denoted by General Formula (1) will be described below, but the present invention is not limited thereto.

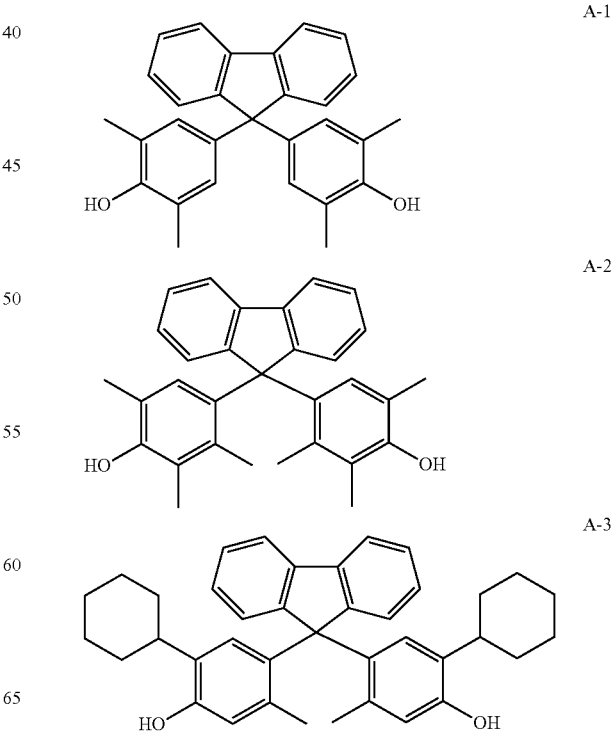

A-4
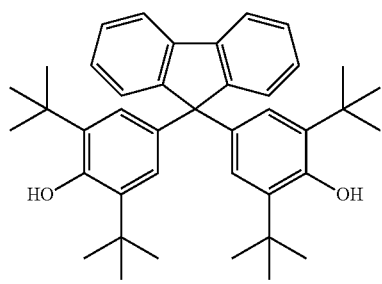
A-5
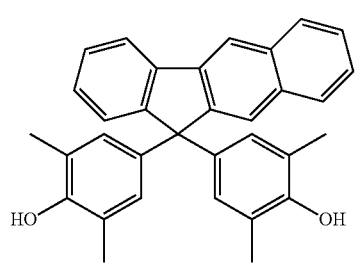
A-6
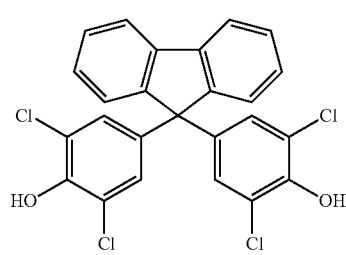
A-7
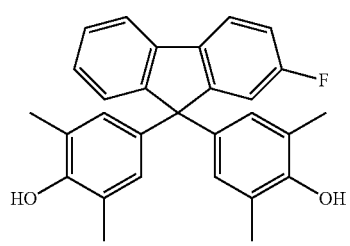
A-8
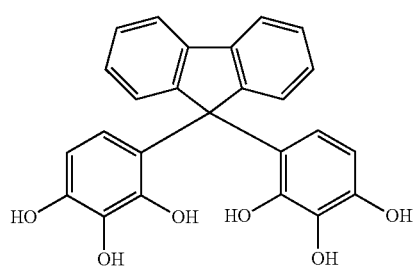
A-9
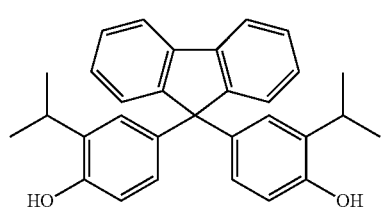
A-10
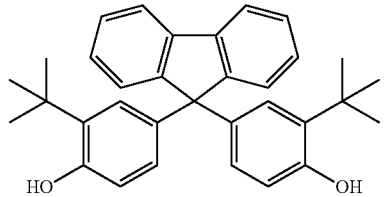
A-11
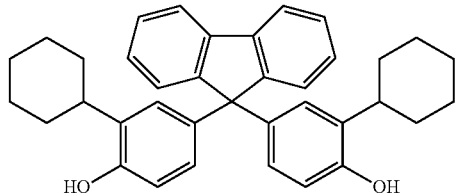
A-12
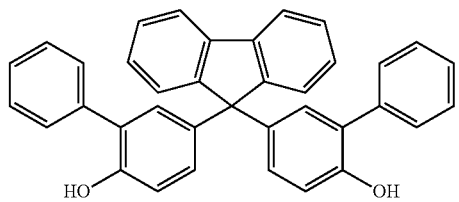
A-13
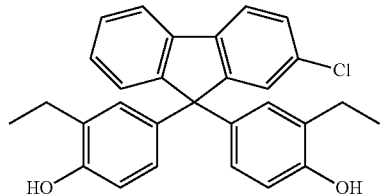
A-14
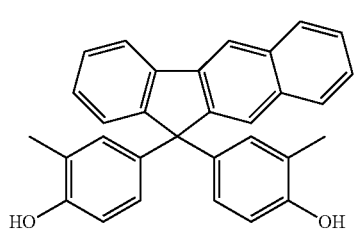
A-15
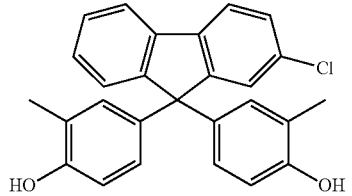
A-16
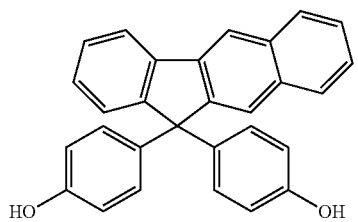

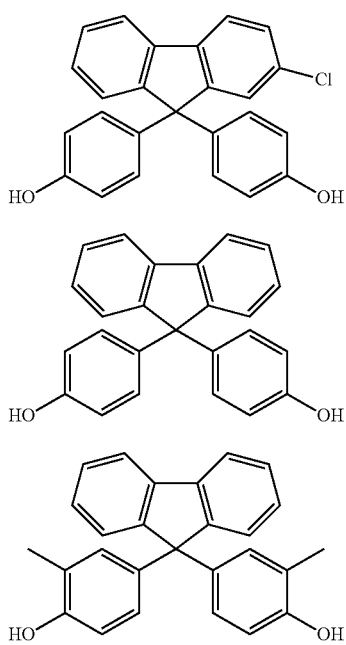

A-17

A-18

A-19

(Manufacturing Method of Compound Denoted by General Formula (1))

The compound denoted by General Formula (1) is able to be obtained by a known method in which fluorenones and phenols are subjected to dehydration condensation in the presence of an acid catalyst. In a dehydration condensation reaction, for example, a mineral acid such as a hydrochloric acid, hydrogen chloride gas, and a sulfuric acid, a methane sulfonic acid, a solid acid, and the like are suitable as the acid catalyst.

(Content of Compound Denoted by General Formula (1))

The content of the compound denoted by General Formula (1) in the (meth)acrylic resin composition of the present invention is preferably greater than or equal to 10 parts by mass, and is more preferably greater than or equal to 20 parts by mass, with respect to 100 parts by mass of the (meth)acrylic resin, from the viewpoint of moisture permeability. In addition, the content is preferably less than or equal to 50 parts by mass, and is more preferably less than or equal to 40 parts by mass, with respect to 100 parts by mass of the (meth)acrylic resin, from the viewpoint of compatibility.

[Compound Preventing Compound Denoted by General Formula (1) from being Oxidized]

The (meth)acrylic resin composition of the present invention contains a compound preventing the compound denoted by General Formula (1) from being oxidized.

A phosphorus-based antioxidant, a phenol-based antioxidant, a sulfur-based antioxidant, or an amide-based antioxidant is able to be preferably used as the compound preventing the compound denoted by General Formula (1) from being oxidized, the phenol-based antioxidant, the sulfur-based antioxidant, and the amide-based antioxidant are more preferable, and the sulfur-based antioxidant is most preferable.

Hereinafter, a specific example of the compound preventing the compound denoted by General Formula (1) from being oxidized will be described, but the present invention is not limited thereto. Furthermore, in B-17 described below, the ratio is a mass ratio.

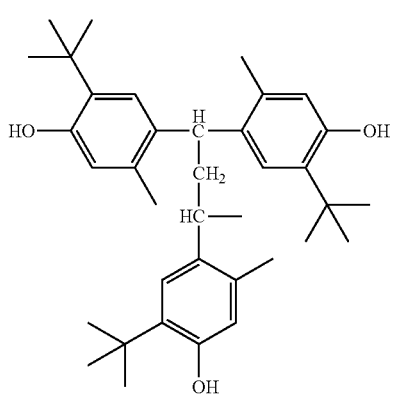

B-1

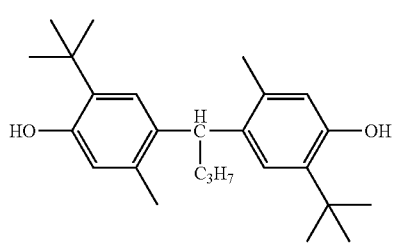

B-2

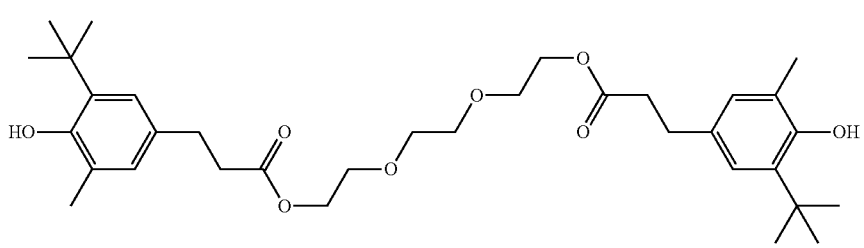

B-3

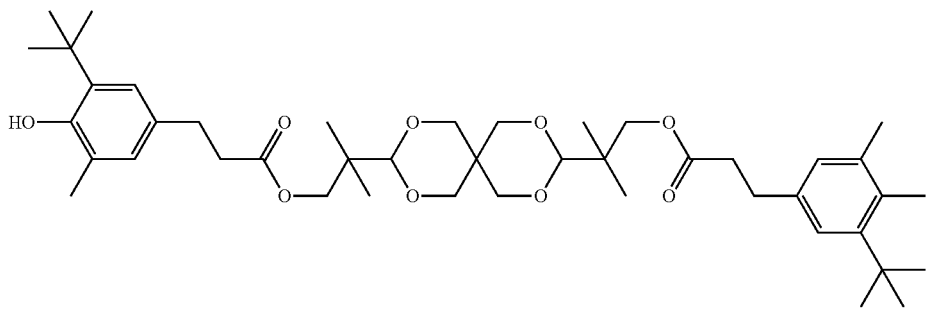
B-4
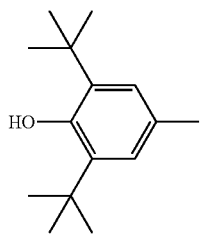
B-5
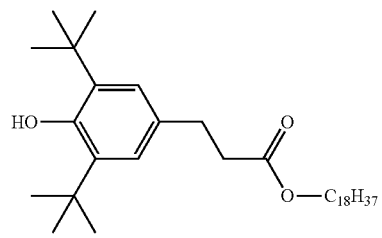
B-6
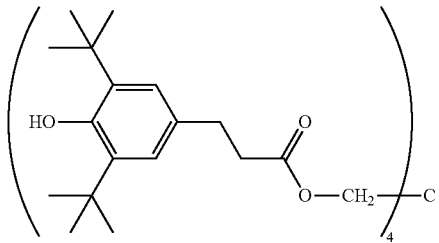
B-7
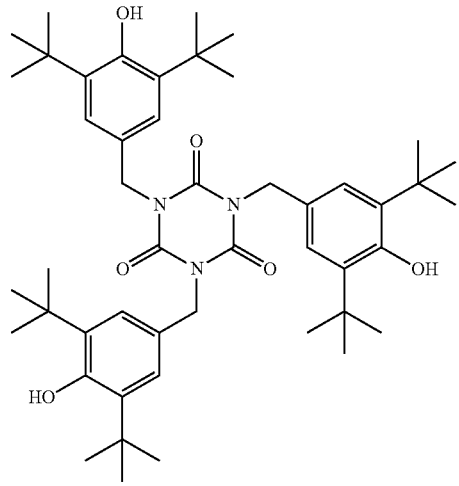
B-8
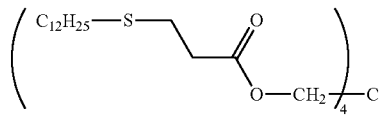
B-9
B-10
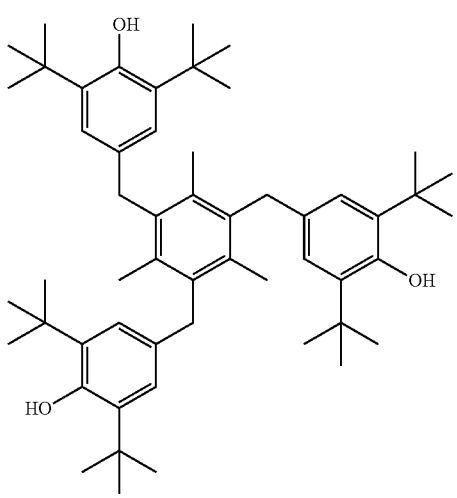

-continued
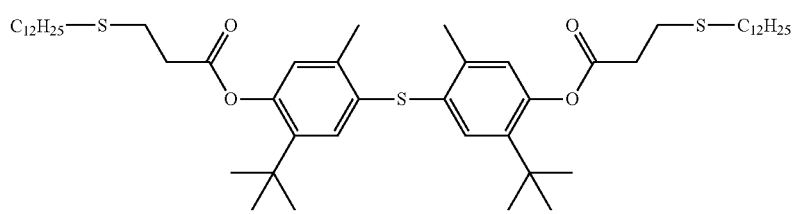
B-11
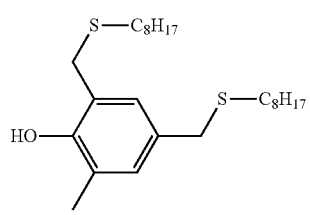
B-12
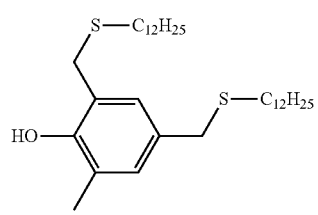
B-13
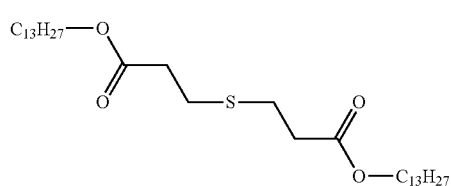
B-14
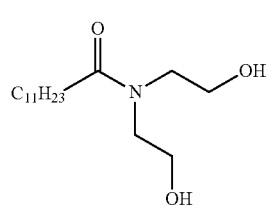
B-15
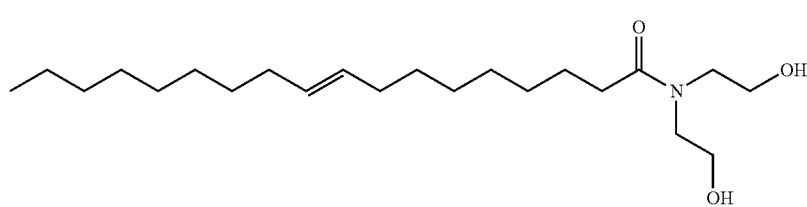
B-16
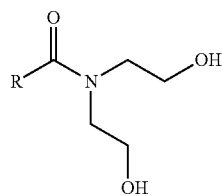
B-17
R = $C_7H_{15}/C_9H_{19}/C_{11}H_{23}/C_{13}H_{27}/C_{14}H_{29}/C_{17}H_{35}/C_{17}H_{33}/C_{17}H_{31}$
= 7.8/7.6/44.8/18.1/9.5/2.4/8.2/1.5
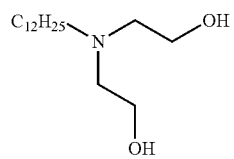
B-18
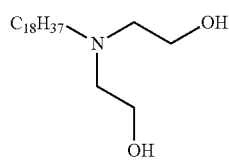
B-19
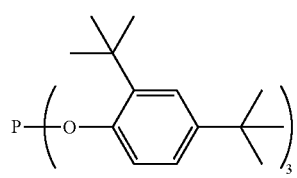
B-20
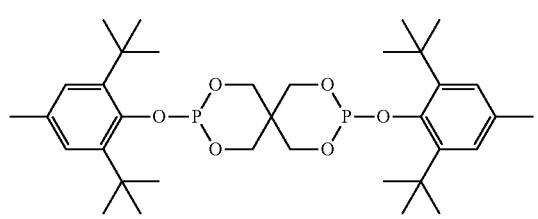
B-21
B-22

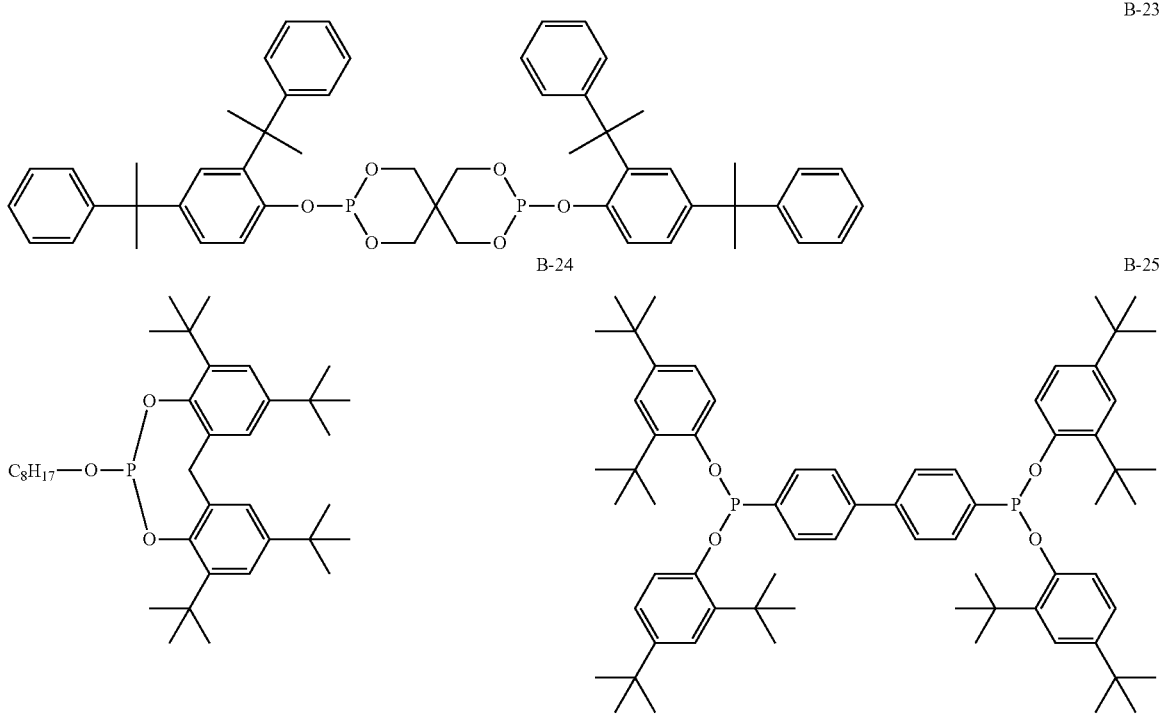

A commercially available compound is able to be preferably used as the compound preventing the compound denoted by General Formula (1) from being oxidized.

The content of the compound preventing the compound denoted by General Formula (1) from being oxidized in the (meth)acrylic resin composition of the present invention is preferably greater than or equal to 0.1 parts by mass, and is more preferably greater than or equal to 0.5 parts by mass, with respect to 100 parts by mass of the compound denoted by General Formula (1), from the viewpoint of preventing oxidization. In addition, the content is preferably less than or equal to 5 parts by mass, and is more preferably less than or equal to 2 parts by mass, with respect to 100 parts by mass of the compound denoted by General Formula (1), from the viewpoint of moisture permeability.

(Additive)

A plasticizer, an ultraviolet absorbent, a brittleness improver, an optical expression agent, and the like are able to be added to the (meth)acrylic resin composition of the present invention as an additive.

The plasticizer has a function of improving fluidity or flexibility of a dope composition. Examples of the plasticizer include a phthalic acid ester-based plasticizer, a fatty acid ester-based plasticizer, a trimellitic acid ester-based plasticizer, a phosphoric acid ester-based plasticizer, a polyester-based plasticizer, an epoxy-based plasticizer, or the like.

Examples of the ultraviolet absorbent include a benzotriazole-based ultraviolet absorbent, a 2-hydroxy benzophenone-based ultraviolet absorbent, a salicylic acid phenyl ester-based ultraviolet absorbent, or the like. For example, triazoles such as 2-(5-methyl-2-hydroxy phenyl) benzotriazole, 2-[2-hydroxy-3,5-bis(α,α-dimethyl benzyl) phenyl]-2H-benzotriazole, and 2-(3,5-di-t-butyl-2-hydroxy phenyl) benzotriazole, and benzophenones such as 2-hydroxy-4-methoxy benzophenone, 2-hydroxy-4-octoxy benzophenone, and 2,2'-dihydroxy-4-methoxy benzophenone are able to be exemplified.

Further, a brittleness improver, an optical expression agent, and the like are also able to be added to the (meth)acrylic resin composition of the present invention as the additive.

Only one type of the additive may be independently used, or two or more types thereof may be used in combination.

[Concentration of Solid Contents in (Meth)Acrylic Resin Composition]

The concentration of solid contents in the (meth)acrylic resin composition is preferably greater than or equal to 10 mass %, and is more preferably less than or equal to 30 mass %. Accordingly, it is possible to obtain a film having high quality in which the unevenness in the film thickness is suppressed. In addition, the concentration of the solid contents in the (meth)acrylic resin composition is preferably less than or equal to 25 mass %, and is more preferably less than or equal to 22 mass %. Accordingly, it is possible to reliably obtain an effect of easily peeling off a film by alcohol described below.

[Solvent]

The (meth)acrylic resin composition may contain a solvent.

The solvent of the (meth)acrylic resin composition may dissolve the (meth)acrylic resin, the compound denoted by General Formula (1), the compound preventing the compound denoted by General Formula (1) from being oxidized, and other additives to be added as necessary, and is not particularly limited. In the present invention, either a chlorine-based solvent containing a chlorine-based organic solvent as a main solvent or a non-chlorine-based solvent not containing a chlorine-based organic solvent is able to be used as an organic solvent. Two or more types of organic solvents may be used by being mixed.

The chlorine-based organic solvent is preferably used as a main solvent at the time of preparing the (meth)acrylic resin composition. In the present invention, the type of chlorine-based organic solvent is not particularly limited insofar as the object is able to be attained in a range where the (meth)acrylic resin and the additive contained in the (meth)acrylic resin composition is able to be dissolved and cast, and thus, a film is able to be formed. The chlorine-based organic solvent is preferably dichloromethane and chloroform. The dichloromethane is particularly preferable. In addition, there is no particular problem even in a case where an organic solvent other than the chlorine-based organic solvent is mixed. In this case, it is necessary that the dichloromethane is used in the amount of at least 50 mass % with respect to the total amount of the organic solvent. Other organic solvents which are used along with the chlorine-based organic solvent in the present invention will be described below. That is, a solvent selected from ester, ketone, ether, alcohol, hydrocarbon, and the like, which have 3 to 12 carbon atoms is preferable as a preferred other organic solvent. The ester, the ketone, the ether, and the alcohol may have a cyclic structure. A compound having two or more of any one of the functional groups (that is, —O—, —CO—, and —COO—) of the ester, the ketone, and the ether is also able to be used as the solvent, and for example, the compound may simultaneously have other functional groups such as an alcoholic hydroxy group. In a case of the solvent having two or more types of functional groups, the number of carbon atoms may be in the defined range of the compound having any one of the functional groups.

Examples of the esters having 3 to 12 carbon atoms include ethyl formate, propyl formate, pentyl formate, methyl acetate, ethyl acetate, pentyl acetate, and the like. Examples of the ketones having 3 to 12 carbon atoms include acetone, methyl ethyl ketone, diethyl ketone, diisobutyl ketone, cyclopentanone, cyclohexanone, methyl cyclohexanone, and the like. Examples of the ethers having 3 to 12 carbon atoms include diisopropyl ether, dimethoxy methane, dimethoxy ethane, 1,4-dioxane, 1,3-dioxolane, tetrahydrofuran, anisole, phenetole, and the like. Examples of the organic solvent having two or more types of functional groups include 2-ethoxy ethyl acetate, 2-methoxy ethanol, 2-butoxy ethanol, and the like.

In addition, the alcohol which is used along with the chlorine-based organic solvent may be preferably straight chain alcohol, branch alcohol, or cyclic alcohol, and in particular, saturated aliphatic hydrocarbon is preferable. A hydroxy group of the alcohol may be any one of a primary hydroxy group to a tertiary hydroxy group. Examples of the alcohol include methanol, ethanol, 1-propanol, 2-propanol, 1-butanol, 2-butanol, t-butanol, 1-pentanol, 2-methyl-2-butanol, and cyclohexanol. Furthermore, fluorine-based alcohol is also used as the alcohol. Examples of the fluorine-based alcohol include 2-fluoroethanol, 2,2,2-trifluoroethanol, 2,2,3,3-tetrafluoro-1-propanol, and the like. Further, the hydrocarbon may be straight chain hydrocarbon, branch hydrocarbon, or cyclic hydrocarbon. Either aromatic hydrocarbon or aliphatic hydrocarbon is able to be used. The aliphatic hydrocarbon may be saturated aliphatic hydrocarbon or unsaturated aliphatic hydrocarbon. Examples of the hydrocarbon include cyclohexane, hexane, benzene, toluene, and xylene.

For example, solvents disclosed in JP2007-140497A are able to be used as other solvents.

The (meth)acrylic resin composition of the present invention contains a mixed solvent of (A) methylene chloride and (B) alcohol having 1 to 4 carbon atoms as the solvent, and it is preferable that the mass ratio (A:B) of the (A) methylene chloride and the (B) alcohol having 1 to 4 carbon atoms is 85:15 to 50:50. Furthermore, in the following description, the methylene chloride will be referred to as a solvent (A), and the alcohol having 1 to 4 carbon atoms will be referred to as a solvent (B).

According to such a solvent composition, in the (meth)acrylic resin composition, it is possible to easily peel off a polymer film which is obtained by drying a casting film from a support.

(Alcohol Having 1 to 4 Carbon Atoms)

It is preferable that methanol, ethanol, and isopropanol are used as the (B) alcohol having 1 to 4 carbon atoms which is used in the mixed solvent, it is more preferable that the methanol and the ethanol are used, and it is particularly preferable that only the methanol is used.

(Mixing Ratio A:B)

The mixing ratio (A:B) of the (A) methylene chloride and the (B) alcohol having 1 to 4 carbon atoms in the solvent is A:B=85:15 to 50:50. The ratio of A:B is preferably 85:15 to 60:40, is more preferably 85:15 to 70:30, and is even more preferably 85:15 to 75:25. By setting the mixing ratio (A:B) to be in such a range, it is possible to reliably obtain the effect of easily peeling off the film as described above.

[Properties of (Meth)Acrylic Resin Composition]

(Drying Speed of (Meth)Acrylic Resin Composition)

The drying speed of the (meth)acrylic resin composition of the present invention is measured in the following procedure.

(1) The (meth)acrylic resin composition is prepared such that the concentration of the (meth)acrylic resin becomes 16 mass %, and the (meth)acrylic resin composition is cast onto a metal support such that the thickness becomes 56 μm.

(2) A polymer film formed by the (meth)acrylic resin composition is peeled off from the metal support at a time point where the amount of residual solvent in the (meth)acrylic resin composition becomes 20 mass %.

(3) Four sides of the peeled polymer film are fixed to a metal frame, and the polymer film is dried in a cell controller at 140° C.

(4) The polymer film is left to stand for 5 minutes, and then, the polymer film is taken out from the cell controller, and thus, a part of the polymer film is sampled as a sample.

(5) The sampled sample is dissolved in a chloroform solution, and the amount of solvent remaining on the sample is quantified by a gas chromatography.

After that, sampling is performed every 5 minutes by repeating (4) and (5), and a calibration curve is drawn, and thus, a time at which the amount of residual solvent becomes less than or equal to 0.1 mass % is confirmed.

The drying time of the (meth)acrylic resin composition is preferably less than 40 minutes, is more preferably less than or equal to 30 minutes, and is even more preferably less than or equal to 25 minutes, from the viewpoint of increasing the manufacturing efficiency of the film. In a dope composition of the present invention, an additive having a weight-average molecular weight of less than 50,000 has a function of accelerating the drying of the casting film, and thus, it is possible to reliably suppress the drying time to be shorter than 40 minutes.

<Film Obtained by Performing Film Formation with Respect to (Meth)Acrylic Resin Composition>

A film obtained by performing film formation with respect to the (meth)acrylic resin composition of the present invention has excellent heat resistance and is able to be efficiently manufactured, and thus, is useful in various applications. In addition, the film has excellent heat resistance and a low haze value, and thus, is able to be preferably used as an optical film such as a polarizing plate protective film or an optical compensation film.

Hereinafter, a polarizing plate protective film (a polarizing plate protective film of the present invention) and an optical compensation film will be described as a preferred application of the film obtained by performing film formation with respect to the (meth)acrylic resin composition of the present invention.

[Polarizing Plate Protective Film]

The polarizing plate protective film of the present invention includes at least one film obtained by performing film formation with respect to the (meth)acrylic resin composition of the present invention, may have a configuration including only one film obtained by performing film formation with respect to the (meth)acrylic resin composition of the present invention, or may have a configuration including two or more films obtained by performing film formation with respect to the (meth)acrylic resin composition of the present invention, and the configuration including only one film obtained by performing film formation with respect to the (meth)acrylic resin composition of the present invention is preferable.

In addition, the polarizing plate protective film of the present invention may have a multilayer configuration including layers other than the film obtained by performing film formation with respect to the (meth)acrylic resin composition of the present invention. In a case of the multilayer configuration including two or more films obtained by performing film formation with respect to the (meth)acrylic resin composition of the present invention, each film may be formed by performing film formation with respect to the same (meth)acrylic resin composition, or may be formed by performing film formation with respect to different (meth)acrylic resin compositions. In addition, in the polarizing plate protective film, the surface of the film obtained by performing film formation with respect to the (meth)acrylic resin composition of the present invention may be subjected to a surface treatment described below, or a functional layer may be disposed on the surface of the film. It is preferable that the polarizing plate protective film of the present invention has a configuration including the film obtained by performing film formation with respect to the (meth)acrylic resin composition of the present invention as at least one outermost layer (a layer including an air boundary).

The configuration of the (meth)acrylic resin composition can be referred to the description in the section of <(Meth) Acrylic Resin Composition> described above. In addition, a film formation method of the (meth)acrylic resin composition will be described in the section of <Manufacturing Method of Polarizing Plate Protective Film> described below.

Here, the properties of the polarizing plate protective film of the present invention will be described in detail.

(Moisture Permeability of Polarizing Plate Protective Film in Terms of 40 μm)

Herein, the "moisture permeability of the polarizing plate protective film in terms of 40 μm" is a standard value obtained by converting the moisture permeability of the film which is measured in conditions of a temperature of 40° C. and relative humidity of 90% as the film thickness of the film of 40 μm on the basis of a method defined in JIS Z-0208. In samples having different film thicknesses, it is necessary that the conversion is performed by setting the criterion to be 40 μm.

Here, in the polarizing plate protective film of the present invention, the film thickness of the film obtained by performing film formation with respect to the (meth)acrylic resin composition of the present invention is preferably 10 μm to 60 μm, is more preferably 10 μm to 50 μm, and is even more preferably 20 μm to 50 μm.

The conversion of the film thickness is performed according to the following numerical expression.

Numerical Expression: Moisture Permeability in terms of 40 μm=Actually Measured Moisture Permeability×Actually Measured Film Thickness (μm)/40 (μm)

In a liquid crystal display device to which the polarizing plate protective film is applied, in order to suppress the warping of a liquid crystal cell or the display unevenness at the time of black display after being aged in an environment of normal temperature, high humidity, and high temperature and high humidity aging, the moisture permeability of the polarizing plate protective film of the present invention in terms of 40 μm is preferably less than or equal to 70 g/m$^2$/day, is more preferably less than or equal to 50 g/m$^2$/day, and is even more preferably less than or equal to 40 g/m$^2$/day.

(Haze Value of Polarizing Plate Protective Film)

Herein, the "haze value" of the polarizing plate protective film is the total haze value and the inside haze value which are measured in film sample cut from the polarizing plate protective film to have a size of 40 mm×80 mm in conditions of a temperature of 25° C. and relative humidity of 60%, on the basis of a method defined in JIS K-6714. The haze value is able to be measured by using a hazemeter (manufactured by Suga Test Instruments Co., Ltd., Product Name of HGM-2DP).

In the polarizing plate protective film of the present invention, it is preferable that the total haze value is less than or equal to 2.00%. In a case where the total haze value is less than or equal to 2.00%, the transparency of the film is high, and an effect of improving the contrast ratio or the brightness of the liquid crystal display device is obtained. The total haze value is more preferably less than or equal to 1.00%, is even more preferably less than or equal to 0.50%, is particularly preferably less than or equal to 0.30%, and is most preferably less than or equal to 0.20%. The optical performance is excellent as the total haze value becomes lower, and in consideration of the selection of a raw material, manufacturing management, or the handling properties of the roll film, it is preferable that the total haze value is greater than or equal to 0.01%.

It is preferable that the inside haze value of the polarizing plate protective film of the present invention is less than or equal to 1.00%. By setting the inside haze value to be less than or equal to 1.00%, it is possible to improve the contrast ratio of the liquid crystal display device, and it is possible to realize excellent display properties. The inside haze value is more preferably less than or equal to 0.50%, is even more preferably less than or equal to 0.20%, is particularly preferably less than or equal to 0.10%, and is most preferably less than or equal to 0.05%. It is preferable that the inside haze value is greater than or equal to 0.01% from the viewpoint of the selection of the raw material or the manufacturing management.

In the polarizing plate protective film of the present invention, it is particularly preferable that the total haze value is less than or equal to 0.30%, and the inside haze value is less than or equal to 0.10%.

The total haze value and the inside haze value are able to be adjusted according to the type or the added amount of the (meth)acrylic resin of the (meth)acrylic resin composition, an ester oligomer, or other additives, the selection of the ester oligomer or the additive (in particular, a weight-average molecular weight and an added amount), and film manufacturing conditions (a temperature, a stretching ratio, and the like at the time of performing stretching).

[Manufacturing Method of Polarizing Plate Protective Film]

Next, a manufacturing method of the polarizing plate protective film of the present invention will be described.

The manufacturing method of the polarizing plate protective film of the present invention is a method of manufacturing a polarizing plate protective film by a solution film formation method, and includes at least a dissolving step of dissolving a material such as a (meth)acrylic resin in a solvent and of preparing the (meth)acrylic resin composition (the dope composition) of the present invention, a casting step of casting the dope composition described above onto a support and of forming a casting film, and a peeling step of drying the casting film described above, and then, of peeling the casting film from the support described above, and of obtaining a film.

As necessary, after the peeling step, a drying step of further drying the peeled film, and of removing a residual solvent (a volatile content) may be further performed.

As necessary, after the peeling step, a stretching step of stretching the film in at least a monoaxial direction, and as necessary, or stretching the film in a biaxial direction may be performed.

Hereinafter, each step will be described.

The steps, for example, are able to be continuously performed by a film manufacturing line illustrated in the FIGURE. Here, a film manufacturing line which is used in the manufacturing method of the present invention is not limited to the film manufacturing line illustrated in FIG. 1. Furthermore, in the film manufacturing line, a "wet film", a "dry film" obtained by drying the wet film, and a "stretching film" obtained by stretching the dry film are obtained in the middle of the line, the casting film of the present invention includes all films after being casted before the peeling step (the "wet film", the "dry film", and the "stretching film"), and the film of the present invention includes all films peeled off from the support after the peeling step (the "wet film", the "dry film", and the "stretching film").

A film manufacturing line 20 illustrated in FIG. 1 includes a stock tank 21, a filtration device 30, a casting die 31, a metal support 34 stretched between rotating rollers 32 and 33, a tenter type drier 35, and the like. Further, a selvage cutting device 40, a drying chamber 41, a cooling chamber 42, a winding chamber 43, and the like are arranged.

A stirrer 61 which is rotated by a motor 60 is attached to the stock tank 21. Then, the stock tank 21 is connected to the casting die 31 through a pump 62 and the filtration device 30.

It is preferable that the width of the casting die 31 is 1.1 times to 2.0 times the width of a film which becomes a final product.

The metal support 34 stretched between the rotating rollers 32 and 33 is disposed in the lower portion of the casting die 31. The rotating rollers 32 and 33 are rotated by a driving device (not illustrated), and the metal support 34 endlessly travels according to the rotation.

In addition, in order to set the surface temperature of the metal support 34 to a predetermined value, it is preferable that a heat-transmitting medium circulation device 63 is attached to the rotating rollers 32 and 33. It is preferable that the surface temperature of the metal support 34 is able to be adjusted to be −20° C. to 40° C.

It is preferable to use the metal support 34 of which the width is in a range of 1.1 times to 2.0 times the casting width of a dope composition 22. In addition, it is preferable that the metal support is ground such that a length is 20 m to 200 m, a film thickness is 0.5 mm to 2.5 mm, and surface roughness is less than or equal to 0.05 μm. It is preferable that the metal support 34 is formed of stainless steel, and it is more preferable that the metal support 34 is formed of SUS316 in order to have sufficient corrosion resistance and strength. In addition, the metal support 34 in which film thickness unevenness of the entire metal support 34 is less than or equal to 0.5% is preferably used.

Furthermore, the rotating rollers 32 and 33 are able to be directly used as the support.

The casting die 31, the metal support 34, and the like are contained in a casting chamber 64. Temperature adjustment equipment 65 for retaining the internal temperature of the casting chamber 64 at a predetermined value, and a condenser 66 for performing condensation collecting with respect to an organic solvent which is volatilized are disposed in the casting chamber 64. Then, a collecting device 67 for collecting the organic solvent which has been subjected to condensation and liquefaction is disposed on the outside of the casting chamber 64. In addition, it is preferable that a decompression chamber 68 for performing pressure control with respect to a back surface portion of a casting bead which is formed from the casting die 31 to the metal support 34 is disposed, and in this embodiment, the decompression chamber 68 is used.

Blowing ports 70, 71, and 72 for evaporating the solvent in a casting film 69 are disposed in the vicinity of the circumferential surface of the metal support 34.

A crossover portion 80 includes a blowing machine 81, a crusher 90 for finely cutting the excess of a side end portion of a cut film 82 (referred to as a selvage) is connected to the selvage cutting device 40 on the downstream of the tenter type drier 35.

The drying chamber 41 includes a plurality of rollers 91, and an adsorption collecting device 92 for performing adsorption collecting with respect to solvent gas generated by being evaporated is attached to the drying chamber 41. A forced static elimination device (a static elimination bar) 93 for adjusting the charging voltage of the film 82 to be in a predetermined range (for example, −3 kV to +3 kV) is disposed on the downstream of the cooling chamber 42. Further, in this embodiment, a knurling applying roller 94 for applying knurling to both edges of the film 82 in embossing processing is suitably disposed on the downstream of the forced static elimination device 93. In addition, a winding roller 95 for winding the film 82, and a press roller 96 for controlling a tension at the time of winding the film are included in the winding chamber 43.

Next, an example of a manufacturing method of the film 82 by using the film manufacturing line 20 (a band manufacturing device) as described above will be described below.

The dope composition 22 consistently becomes even by rotating the stirrer 61. An additive such as a retardation expression agent, a plasticizer, and an ultraviolet absorbent is able to be mixed into the dope composition 22 even at the time of being stirred.

(1) Dissolving Step

The dissolving step is a step of preparing the (meth)acrylic resin composition (the dope composition) of the present invention. It is preferable that the dissolving step of the present invention is a step of forming a dope by dissolving a polymer in an organic solvent mainly containing a good solvent with respect to a polymer in a dissolution pot while stirring an additive, or a step of forming a dope composition by mixing an additive solution into a polymer solution.

The material of the dope composition can be referred to the description in the section of <(Meth)Acrylic Resin Composition> described above.

It is preferable that the dope composition is adjusted at a temperature of higher than or equal to 0° C. (a normal temperature or a high temperature). The dope composition of the present invention is able to be prepared by using a dope preparation method and a device in a general solvent casting method.

The polymer is able to be dissolved by using various dissolving methods such as a method of dissolving the polymer at normal pressure, a method of dissolving the polymer at a temperature lower than or equal to a boiling point of the main solvent, a method of dissolving the polymer at a temperature of higher than or equal to the boiling point of the main solvent under pressurization, a method using a cooling dissolving method as disclosed in JP1997-95544A (JP-H09-95544A), JP1997-95557A (JP-H09-95557A), or JP1997-95538A (JP-H09-95538A), and a method of dissolving the polymer at high pressure as disclosed in JP1999-21379A (JP-HI 1-21379A). The method of dissolving the polymer at a temperature of higher than or equal to the boiling point of the main solvent under pressurization is particularly preferable from the viewpoint of dissolution efficiency. In this case, the (meth)acrylic resin, the solvent (A), and the solvent (B) are put into a pressurization container, the pressurization container is sealed, and the (meth)acrylic resin, the solvent (A), and the solvent (B) are stirred while being heated to a temperature in a range of higher than or equal to the boiling point of the solvent at normal temperature, in which the solvent is not boiled, under pressurization.

The temperature in a case of performing heating us generally higher than or equal to 40° C., is preferably 60° C. to 200° C., and is more preferably 80° C. to 110° C.

It is preferable that the concentration of the (meth)acrylic resin in the dope composition is 10 mass % to 40 mass %. It is preferable that an additive is added to the dope composition during the dissolution or after the dissolution, and is dissolved and dispersed, and then, is filtered through a filter material, is defoamed, and is fed to the next step by a liquid feeding pump.

(2) Casting Step

The casting step is a step of forming the casting film by casting the dope composition described above onto the metal support. It is preferable that the casting step is a step of feeding the dope to a pressurizing die through a liquid feeding pump (for example, a pressurizing quantitative gear pump), and of casting the dope composition in a casting position on the metal support of an endless metal belt performing infinite feeding, for example, a stainless steel belt, a rotating metal drum, or the like, from a pressurizing die slit. The dope composition 22 is fed to the filtration device 30 by the pump (For example, the pressurizing quantitative gear pump) 62, and is filtered, and then, is cast onto the metal support 34 from the casting die 31.

The casting bead is formed from the casting die 31 to the metal support 34, and the casting film 69 is formed on the metal support 34. It is preferable that the temperature of the dope composition 22 at the time of performing casting is −10° C. to 57° C.

The casting film 69 is moved according to the movement of the metal support 34. The pressurizing die in which a slit shape of a base portion of the die is able to be adjusted, and a film thickness easily becomes even is preferable as the die. Examples of the pressurizing die include a coat hanger die, a T die, and the like, and any of them is preferably used. The surface of the metal support is a mirror surface. In order to increase a film formation speed, two or more pressurizing dies may be disposed on the metal support, and the amount of dope composition may be layered by being divided. Alternatively, it is preferable that a film having a laminated structure is obtained by a co-casting method of simultaneously casting a plurality of dope compositions.

(3) Solvent Evaporating Step

Next, the casting film 69 is continuously transported to a portion on which a blowing port 73 is arranged. Dry air from a nozzle of the blowing port 73 is blown towards the casting film 69. It is preferable that a solvent evaporating step is provided between the casting step and the peeling step. The solvent evaporating step is a step of heating the casting film (also referred to as a web: a state before being a finished product of a polymer film, a casting film still containing a large amount of solvent is referred to as a web) on the metal support, and of evaporating the solvent until the web is able to be peeled off from the metal support.

In order to evaporate the solvent, a method of blowing air from the web side and/or a method of performing heat-transmitting from the back surface of the metal support by a liquid, a method of performing heat-transmitting from the front side and the back side by radiation heat, and the like are used, and the method of performing the heat-transmitting from the back surface by the liquid is preferable since drying efficiency is excellent. In addition, a method in which the methods are combined is also preferable. In a case of performing the heat-transmitting from the back surface by the liquid, it is preferable that heating is performed at a temperature lower than or equal to the boiling point of the main solvent in the organic solvent used in the dope composition or the boiling point of the organic solvent having the lowest boiling point.

(4) Peeling Step

The peeling step is a step of drying the casting film described above, and then, of peeling the casting film from the support described above, and of obtaining a film. The solvent is evaporated by being dried, and thus, the casting film 69 becomes a polymer film having self-supporting properties, and then, is peeled off from the metal support 34 while being supported by a peeling roller 75 as a polymer film 74. It is preferable that the peeling step is a step of peeling off the web from which the solvent is evaporated on the metal support in a peeling position. The peeled web is fed to the next step. Furthermore, in a case where the amount of residual solvent of the web at the time of being peeled off (the following expression) excessively increases, the web is hardly peeled off, and in contrast, in a case where the web is peeled off after being excessively sufficiently dried on the metal support, a part of the web is peeled off in the middle.

It is preferable that the peeling is performed in a range where the amount of residual solvent of the web on the metal support at the time of peeling off the web is 5 mass % to 150 mass % according to drying conditions, the length of the metal support, or the like, and in a case of performing the peeling at a time point where the amount of residual solvent is large, the amount of residual solvent at the time of peeling off the web is determined according to a balance between an economic speed and quality. In the present invention, the temperature in the peeling position on the metal support is preferably −50° C. to 40° C., is more preferably 10° C. to 40° C., and is most preferably 15° C. to 30° C.

In addition, the amount of residual solvent of the web in the peeling position is preferably 10 mass % to 150 mass %, and is more is preferably 10 mass % to 120 mass %.

The amount of residual solvent is able to be denoted by the following expression.

$$\text{Amount of Residual Solvent (mass \%)} = [(M-N)/N] \times 100$$

Here, M represents the mass of the web at an arbitrary time point, and N represents the mass of the web having a mass M at the time of being dried at 110° C. for 3 hours.

The wet film 74 is peeled off in such conditions, and then, the polymer film 74 is fed into the tenter type drier 35 by transporting the crossover portion 80 in which a plurality of rollers are disposed. In the crossover portion 80, drying air at a desirable temperature is blown from the blowing machine 81, and thus, the polymer film 74 is dried. At this time, it is preferable that the temperature of the drying air is 20° C. to 250° C.

It is preferable that the polymer film 74 is stretched in a width direction (a TD direction) which is orthogonal to a transport direction (an MD direction). According to the stretching in the width direction, unevenness which occurs at the time of drying the web and at the time of peeling off the web on the support is able to be reduced, and an excellent film shape is able to be obtained in the surface of the film. A stretching ratio in the width direction is preferably greater than or equal to 10%, is more preferably greater than or equal to 20%, and is even more preferably greater than or equal to 30%.

(5) Drying or Heat Treatment Step, and Stretching Step

After the peeling step described above, it is preferable that the web is dried by using a drying device in which the web is alternately transported through a plurality of rollers arranged in the drying device, and/or a tenter device in which the web is transported by clipping both ends of the web with a clip.

The polymer film 74 which is fed to the tenter type drier 35 is dried while being transported by gripping both end portions of the polymer film 74 with a clip. At this time, the stretching in the width direction is able to be performed by the tenter type drier 35.

Furthermore, the inside of the tenter type drier 35 is sectionally divided into a temperature zone, and drying conditions are able to be suitably adjusted for each section.

Thus, the polymer film 74 is able to be stretched in the width direction by the crossover portion 80 and/or the tenter type drier 35.

The stretching may be performed in the transport direction, and the rotation speed of the roller on the downstream side is faster than the rotation speed of the roller on the upstream side by crossover portion 80, and thus, the stretching is able to be performed in the transport direction by applying a draw tension to the polymer film 74.

Here, in the crossover portion 80 and/or the tenter type drier 35, the polymer film 74 may be dried in an un-stretched state, the amount of residual solvent in the film may be set to be less than or equal to 3.0 mass %, preferably less than or equal to 1.0 mass %, more preferably less than or equal to 0.5 mass %, even more preferably less than or equal to 0.3 mass %, and particularly preferably less than or equal to 0.2 mass %, and then, the stretching may be performed.

Furthermore, in a case where a polymer film in which the amount of residual solvent is less than or equal to 3.0 mass % is stretched, the polymer film may be wound once in an un-stretched state, and then, the stretching may be performed.

Blowing hot air to both surfaces of the web is general as means for performing drying and a heat treatment, and means for heating the web by being brought into contact with a microwave instead of air is also used. A temperature, an air volume, and a time are different according to the solvent to be used, and conditions may be suitably selected according to the type of solvent to be used, and a combination thereof.

The polymer film to be stretched may be a dry film or a wet film, and it is more preferable that the polymer film is a wet film.

A stretching treatment may be performed in any one direction of MD and TD, or biaxial stretching may be performed in both directions. The stretching in the direction of each of MD and TD may be performed in one stage, or may be performed in a multistage. In a case of performing the biaxial stretching, it is preferable that the stretching is performed in the order of MD and TD.

First, stretching in a film transport direction MD will be described.

The stretching ratio of the stretching in the film transport direction MD is preferably 30% to 80%, and is particularly preferably 40% to 60%. The stretching ratio (extension) of the web at the time of performing stretching is able to be attained according to a difference in the circumferential speed of the speed of the metal support and the peeling speed (the drawing of the peeling roll). For example, in a case where a device including two nip rolls is used, the rotation speed of the nip roller on an outlet side is faster than the rotation speed of the nip roll on an inlet side, and thus, it is possible to preferably stretch the film in the transport direction (a vertical direction).

Furthermore, here, the "stretching ratio (%)" indicates a value obtained by the following expression.

$$\text{Stretching Ratio (\%)} = 100 \times ((\text{Length after Stretching}) - (\text{Length before Stretching}))/\text{Length before Stretching}$$

At this time, it is preferable that a surface temperature T1 of the film is in the following range in order to perform stretching without breaking the film.

$$T1 \leq 100° \text{C.} - 3.2 A1$$

Here, A1 is the amount of residual solvent in the web at the time of performing the stretching in MD, is preferably 10 mass % to 30 mass %, and is more preferably 10 mass % to 20 mass %.

On the other hand, it is preferable that the surface temperature T1 of the film is in the following range in order to increase the number of times of folding endurance of the film.

$$T1 \leq 170° \text{C.} - 2.8 A1$$

Next, stretching in the direction TD which is orthogonal to the film transport direction will be described.

The stretching ratio of the stretching in the direction TD which is orthogonal to the film transport direction is preferably 30% to 80%, and is particularly preferably 40% to 60%.

Furthermore, in the present invention, a method of performing stretching by using a tenter device is preferable as a method of performing the stretching in the direction TD which is orthogonal to the film transport direction.

At this time, a surface temperature T2 of the film is in the following range in order to perform stretching without breaking the film.

$$T2 \leq 100° \text{C.} - 3.2 A2$$

Here, A2 is the amount of residual solvent in the web at the time of performing the stretching in TD, is preferably 0 mass % to 10 mass %, and is more preferably 0 mass % to 5 mass %. On the other hand, it is preferable that the surface temperature T2 of the film is in the following range in order to increase the number of times of folding endurance of the film.

$$T2 \leq 170°\text{ C.} - 2.8 A2$$

Furthermore, the web may be dried after the stretching step. In a case where the web is dried after the stretching step, a drying temperature, a drying air volume, and a drying time are different according to the solvent to be used, and drying conditions may be suitably selected according to the type of solvent to be used, and a combination thereof.

Thus, the stretching treatment may be performed in a drying step through the crossover portion 80 and the tenter type drier 35 after the polymer film 74 is formed, or may be performed by drying and then winding the polymer film 74. In a case where an un-stretched film is prepared, the casting of the present invention is preferably performed in conditions where the film thickness of the film is 10 µm to 200 µm, is more preferably performed in conditions where the film thickness of the film is 10 µm to 150 µm, is even more preferably performed in conditions where the film thickness of the film is 10 µm to 100 µm, and is most preferably performed in conditions where the film thickness of the film is 10 µm to 60 µm.

The polymer film 74 is dried by the tenter type drier 35 until a predetermined amount of residual solvent (the volatile content) is obtained, and then, is fed to the downstream side as the film 82. Both edges in both side end portions of the film 82 are cut by the selvage cutting device 40. The cut side end portion is fed to the crusher 90 by a cutter blower (not illustrated). The side end portion of the film is pulverized by the crusher 90, and becomes a chip. The chip is reused for preparing the dope composition, and thus, this method is effective from the viewpoint of cost. Furthermore, a cutting step of both side end portions of the film is able to be omitted, and it is preferable that the cutting step is performed in any one step from the casting step described above to the step of winding the film described above.

The film 82 of which both side end portions are cut and removed is fed to the drying chamber 41, and is dried. It is preferable that the temperature in the drying chamber 41 is in a range of 50° C. to 160° C. In the drying chamber 41, the film 82 is transported while being wound around a roller 91, and here, solvent gas generated by being evaporated is adsorbed and collected by the adsorption collecting device 92. Air from which a solvent component is removed is blown again into the drying chamber 41 as the dry air. Furthermore, in order to change a drying temperature, it is more preferable that the drying chamber 41 is divided into a plurality of sections.

The film 82 is cooled to approximately room temperature by the cooling chamber 42. Furthermore, a humidity control chamber (not illustrated) may be disposed between the drying chamber 41 and the cooling chamber 42. In a case where the humidity control chamber is disposed, it is preferable that air which is adjusted to have desired humidity and temperature is blown with respect to the film 82. Accordingly, the occurrence of curling in the film 82 or the occurrence of winding failure at the time of winding is able to be suppressed.

Further, in the present invention, it is preferable that knurling is applied onto at least one end of the film 82 in embossing processing by disposing the knurling applying roller 94. The width of the knurling is preferably 3 mm to 50 mm, and is more preferably 5 mm to 30 mm, and the height of the knurling is preferably 0.5 µm to 500 µm, and is more preferably 1 µm to 200 µm. The knurling may be one side pressing, or may be both sides pressing.

(6) Winding

Finally, the film 82 is wound around the winding roller 95 in the winding chamber 43. At this time, it is preferable that the film 82 is wound while applying a desired tension to the film 82 by the press roller 96. Furthermore, it is more preferable that the tension is gradually changed from the start of the winding to the end of the winding. The length of the film 82 which is obtained as described above and is wound is preferably 100 m to 10,000 m, is more preferably 500 m to 7,000 m, and is even more preferably 1,000 m to 6,000 m, per one roll. The width of the film is preferably 0.5 m to 5.0 m, is more preferably 1.0 m to 3.0 m, and is even more preferably 1.0 m to 2.5 m. It is preferable that the knurling is applied onto at least one end at the time of winding, and the width of the knurling is preferably 3 mm to 50 mm, and is more preferably 5 mm to 30 mm, and the height of the knurling is preferably 0.5 µm to 500 µm, and is more preferably 1 µm to 200 µm. The knurling may be one side pressing, or may be both sides pressing.

The web obtained as described above is wound, and thus the polarizing plate protective film of the present invention is able to be obtained.

In the solution film formation method, when the dope composition is cast, two or more types of dope compositions are able to be subjected to simultaneously laminating co-casting or sequentially laminating co-casting. Further, both co-castings may be combined. At the time of performing the simultaneously laminating co-casting, a casting die to which a feed block is attached may be used, or a manifold type casting die may be used. It is possible to obtain a film formed of a plurality of layers by the co-casting. In a film formed of a plurality of layers, it is preferable that at least one of the thickness of a layer on an air surface side or the thickness of a layer on the support side is 0.5% to 30% of the film thickness of the entire film. Further, in a case where the simultaneously laminating co-casting is performed, it is preferable that a dope composition having high viscosity is wrapped by a dope composition having low viscosity at the time of casting the dope composition from the die slit onto the support.

The structure of the casting die, the decompression chamber, the metal support, or the like, the co-casting, a peeling method, the stretching, the drying conditions of each of the steps, a handling method, the curling, a winding method after flatness correction, a solvent collecting method, and a film collecting method are specifically disclosed in paragraph [0617] to paragraph [0889] of JP2005-104148A.

In addition, in the above description, an example of the manufacturing method of the polarizing plate protective film of the present invention has been described by using an example in which the dope composition is cast onto the band in the casting step, the same mechanism is established even in a case where the dope composition is cast onto a drum in the casting step. In this case, a device and manufacturing conditions disclosed in JP2013-82192A are preferably used.

[Optical Compensation Film]

The film obtained by performing film formation with respect to the (meth)acrylic resin composition of the present invention is able to be used in various application in addition to the polarizing plate protective film as described above. For example, the film is also able to be preferably used as an optical compensation film of the liquid crystal display device. Furthermore, in general, the optical compensation film indicates a film which is used in the liquid crystal display device and is formed of an optical material compensating retardation, and has the same meaning as that of a retardation plate, an optical compensation sheet, and the like. The optical compensation film has birefringence, and thus, is used for removing the coloration on a display screen of a liquid crystal display device or for improving view angle properties.

The film itself obtained by performing film formation with respect to the (meth)acrylic resin composition of the present invention may be the optical compensation film, or an optically anisotropic layer may be disposed on the optical compensation film by using the optical compensation film as a support. The optically anisotropic layer is not limited by the optical performance or the driving mode of the liquid crystal cell of the liquid crystal display device in which an optical film of the present invention is used, and any optically anisotropic layer which is required as the optical compensation film is also able to be used together. The optically anisotropic layer to be used together may be formed of a composition containing a liquid crystal compound, or may be formed of a thermoplastic film having birefringence.

[Configuration Added to Film]

The film itself obtained by performing film formation with respect to the (meth)acrylic resin composition of the present invention may have an additional configuration according to the application thereof. Examples of such a configuration are able to include a surface treatment which is performed with respect to the surface of the film, a functional layer which is disposed on the surface of the film, and the like. Hereinafter, the surface treatment and the functional layer will be described.

(Surface Treatment)

In the film itself obtained by performing film formation with respect to the (meth)acrylic resin composition of the present invention, a surface treatment is performed according to a case, and thus, improvement in adhesiveness between the film and other layers (for example, a polarizer, an undercoat layer, and a back layer) is able to be attained. For example, a glow discharge treatment, an ultraviolet ray irradiation treatment, a corona treatment, a flame treatment, and an acid or alkali treatment are able to be used. Here, the glow discharge treatment may be low temperature plasma treatment which is performed under low pressure gas of $10^{-3}$ Torr to 20 Torr, and a plasma treatment which is performed under atmospheric pressure is more preferable. Plasma excitable gas indicates gas which is subjected to plasma excitation in the conditions as described above, and examples of the plasma excitable gas include chlorofluorocarbons such as argon, helium, neon, krypton, xenon, nitrogen, carbon dioxide, and tetrafluoromethane and a mixture thereof, and the like. The details thereof are specifically disclosed in pages 30 to 32 of Journal of Technical Disclosure of Japan Institute for Promoting Invention and Innovation (Technical Disclosure No. 2001-1745, published on Mar. 15, 2001 by Japan Institute for Promoting Invention and Innovation), and are preferably used in the present invention.

(Functional Layer)

In addition, a functional layer having a film thickness of 0.1 μm to 20 μm may be laminated on at least one surface of the polarizing plate protective film of the present invention. The type of functional layer is not particularly limited, and includes a hardcoat layer, an antireflection layer (a layer of which the refractive index is adjusted, such as a layer of adjusting a refractive index such as a layer of low refractive index, a layer of intermediate refractive index, and a layer of high refractive index), an antiglare layer, an antistatic layer, an ultraviolet ray absorption layer, a moisture permeability reducing layer, and the like.

The functional layer may be one layer, or may be a plurality of layers. A lamination method of the functional layer is not particularly limited, but it is preferable that the functional layer is disposed by being co-cast with the (meth)acrylic resin composition of the present invention for forming the film described above, or is disposed by being coated onto the film described above formed by using the (meth)acrylic resin composition of the present invention.

In a case where the functional layer is formed by coating and drying, it is preferable that a monomer having an ethylenically unsaturated group is used as a binder. The monomer may be monofunctional or polyfunctional. Among them, it is preferable that a polymerizable polyfunctional monomer is used, it is more preferable that a photopolymerizable polyfunctional monomer is used, and it is particularly preferable that a coating liquid containing a monomer having two or more (meth)acryloyl groups is used.

Specific examples of the monomer having two or more (meth)acryloyl groups are able to include (meth)acrylic acid diesters of alkylene glycol such as neopentyl glycol acrylate, 1,6-hexanediol (meth)acrylate, and propylene glycol di(meth)acrylate; (meth)acrylic acid diesters of polyoxy alkylene glycol such as triethylene glycol di(meth)acrylate, dipropylene glycol di(meth)acrylate, polyethylene glycol di(meth)acrylate, and polypropylene glycol di(meth)acrylate; (meth)acrylic acid diesters of polyhydric alcohol such as pentaerythritol di(meth)acrylate; (meth)acrylic acid diesters of an ethylene oxide adduct or a propylene oxide adduct such as 2,2-bis {4-(acryloxy.diethoxy) phenyl} propane and 2-2-bis{4-(acryloxy.polypropoxy) phenyl} propane; and the like.

Further, epoxy (meth)acrylates, urethane (meth)acrylates, and polyester (meth)acrylates are also preferably used as the photopolymerizable polyfunctional monomer.

Among them, esters of polyhydric alcohol and a (meth)acrylic acid are preferable. The polyhydric alcohol indicates dihydric or more alcohol.

A polyfunctional monomer having three or more (meth)acryloyl groups in one molecule is more preferable. Examples of the polyfunctional monomer having three or more (meth)acryloyl groups in one molecule include pentacrythritol tetra(meth)acrylate, pentaerythritol tri(meth)acrylate, trimethylol propane tri(meth)acrylate, ethylene oxide-modified trimethylol propane tri(meth)acrylate, propylene oxide-modified trimethylol propane tri(meth)acrylate, ethylene oxide-modified phosphoric acid tri(meth)acrylate, trimethylol ethane tri(meth)acrylate, ditrimethylol propane tetra(meth)acrylate, dipentaerythritol tetra(meth)acrylate, dipentaerythritol penta(meth)acrylate, dipentaerythritol hexa(meth)acrylate, 1,2,3-cyclohexane tetramethacrylate, polyurethane polyacrylate, polyester polyacrylate, caprolactone-modified tris(acryloxy ethyl)isocyanurate, and the like.

Further, examples of a resin having three or more (meth)acryloyl groups include an oligomer, a prepolymer, or the like of a polyester resin, a polyether resin, an acrylic resin, an epoxy resin, an urethane resin, an alkyd resin, a spiroacetal resin, a polybutadiene resin, and a polythiol polyene resin which have a comparatively low molecular weight, and a polyfunctional compound such as polyhydric alcohol.

For example, a dendrimer disclosed in JP2005-76005A and JP2005-36105A is able to be used as the other polyfunctional monomer described above.

In addition, esters of polyhydric alcohol and a (meth)acrylic acid, and amides of polyhydric alcohol and isocyanate having a plurality of (meth)acryloyl groups are also preferably used as the polyfunctional monomer.

Aliphatic alcohol is preferable as the polyhydric alcohol, and in particular, alcohol having a cyclic aliphatic hydrocarbon group is more preferable. A cycloalkyl group having 3 to 8 carbon atoms is preferable as an aliphatic group of monocyclic alicyclic alcohol, and examples of the cycloalkyl group having 3 to 8 carbon atoms are able to include a cyclopentyl group, a cyclohexyl group, a cyclobutyl group, a cyclooctyl group, and the like.

Examples of an aliphatic group of polycyclic alicyclic alcohol are able to include a group having a bicyclo structure, a tricyclo structure, a tetracyclo structure, and the like which have carbon atoms of greater than or equal to 5, a cycloalkyl group having 6 to 20 carbon atoms is preferable, and examples of the cycloalkyl group having 6 to 20 carbon atoms are able to include an adamantyl group, a norbornyl group, a dicyclopentyl group, a tricyclodecanyl group, a tetracyclododecyl group, a center skeleton of a compound disclosed in claims of JP2006-215096A, a center skeleton of a compound disclosed in JP2001-10999A, and the like. Furthermore, a part of the carbon atoms in the cycloalkyl group may be substituted with a hetero atom such as an oxygen atom.

Among them, polyhydric alcohols having the adamantyl group, the norbornyl group, the dicyclopentyl group, the tricyclodecanyl group, the tetracyclododecyl group, the center skeleton of the compound disclosed in claims of JP2006-215096A, and the center skeleton of the compound disclosed in JP2001-10999A are particularly preferable as polycyclic alcohol, from the viewpoint of decreasing moisture permeability.

Two or more types of polymerizable polyfunctional monomers may be used in combination. The monomer having such an ethylenically unsaturated group is able to be polymerized by performing irradiation of ionizing radiation or heating in the presence of a photoradical initiator or a thermal radical initiator.

It is preferable that the photopolymerization initiator is used in a polymerization reaction of the photopolymerizable polyfunctional monomer. A photoradical polymerization initiator and a photocationic polymerization initiator are preferable as the photopolymerization initiator, and the photoradical polymerization initiator is particularly preferable.

In addition, it is preferable that the polymerizable polyfunctional monomer described above and a monofunctional monomer are used in combination.

A monomer having one (meth)acryloyl group is preferable as the monofunctional monomer, and in general, the monomer having one (meth)acryloyl group is able to be obtained from monohydric alcohol and an acrylic acid.

The monohydric alcohol described above may be aromatic alcohol, or may be aliphatic alcohol.

Examples of the monohydric alcohol include methyl alcohol, n-propyl alcohol, iso-propyl alcohol, n-butyl alcohol, tert-butyl alcohol, n-amyl alcohol, diacetone alcohol, l-methoxy-2-propanol, furfuryl alcohol, 2-octanol, 2-ethyl hexanol, nonanol, n-decanol, undecanol, n-dodecanol, trimethyl nonyl alcohol, benzyl alcohol, phenethyl alcohol, ethylene glycol monoisoamyl ether, ethylene glycol monophenyl ether, ethylene glycol monobenzyl ether, and ethylene glycol monohexyl ether.

In addition, an aliphatic portion of the aliphatic alcohol may be a cyclic aliphatic portion. The cyclic aliphatic portion may be a monocyclic aliphatic portion, or may be a polycyclic aliphatic portion, and in a case of the polycyclic aliphatic portion, the aliphatic portion may be a bridged aliphatic portion. A cycloalkyl group having 3 to 8 carbon atoms is preferable as the monocyclic aliphatic portion, and examples of the cycloalkyl group having 3 to 8 carbon atoms are able to include a cyclopentyl group, a cyclohexyl group, a cyclobutyl group, a cyclooctyl group, and the like. Examples of the polycyclic aliphatic portion are able to include a group having a bicyclo structure, a tricyclo structure, a tetracyclo structure, and the like which have carbon atoms of greater than or equal to 5, a cycloalkyl group having 6 to 20 carbon atoms is preferable, and examples of the cycloalkyl group having 6 to 20 carbon atoms are able to include an adamantyl group, a norbornyl group, a dicyclopentyl group, a tricyclodecanyl group, a tetracyclododecyl group, a center skeleton of a compound disclosed in claims of JP2006-215096A, a center skeleton of a compound disclosed in JP2001-10999A, and the like. Furthermore, a part of the carbon atoms in the cycloalkyl group may be substituted with a hetero atom such as an oxygen atom.

The monohydric alcohol may be aromatic alcohol, or may be aliphatic alcohol, and monohydric alcohol having greater than or equal to 6 carbon atoms is preferable.

An acrylic acid and a methacrylic acid are preferable as the (meth)acrylic acid.

In addition, in order to use the antireflection layer (the layer of adjusting a refractive index such as the layer of low refractive index, the layer of intermediate refractive index, and the layer of high refractive index), the antiglare layer, the antistatic layer, the ultraviolet ray absorption layer, and the moisture permeability reducing layer as the functional layer, various adducts may be added.

The thickness of the functional layer is preferably 0.01 µm to 100 µm, and is particularly preferably 0.02 µm to 50 µm. Further, a functional layer having a thickness of 0.1 µm to 20 µm is more particularly preferable as the functional layer of reducing moisture permeability.

In a case where the functional layer is set to a functional layer of reducing the moisture permeability, a ratio (C/D) of moisture permeability (C) of an optical film in which the functional layer is laminated to moisture permeability (D) of an optical film in which the functional layer is not laminated is preferably less than or equal to 0.9. The ratio (C/D) is more preferably less than or equal to 0.85, and is even more preferably less than or equal to 0.8.

<Polarizing Plate>

Next, a polarizing plate of the present invention will be described.

The polarizing plate of the present invention includes the polarizing plate protective film of the present invention. The configuration of the polarizing plate protective film of the present invention can be referred to the description in the section of [Polarizing Plate Protective Film] described above.

The polarizing plate is able to be prepared by a general method. Examples of a preparation method of the polarizing plate include a method in which the polarizing plate protective film of the present invention is subjected to an alkali treatment, and is bonded to both surfaces of a polarizer which is prepared by dipping and stretching a polyvinyl alcohol film in an iodine solution by using an aqueous solution of completely saponified polyvinyl alcohol. Easily adhesive processing as disclosed in JP1994-94915A (JP-H06-94915A) and JP1994-118232A (JP-H06-118232A)

may be performed instead of the alkali treatment. In addition, the surface treatment described above may be performed.

Example of an adhesive which is used for bonding the treatment surface of the polarizing plate protective film to the polarizer include a polyvinyl alcohol-based adhesive such as polyvinyl alcohol and polyvinyl butyral, a vinyl-based latex such as butyl acrylate, and the like.

The polarizing plate protective film and the polarizer may be bonded by other adhesives or pressure sensitive adhesives, or may be directly laminated without using the adhesive or the pressure sensitive adhesive.

<Liquid Crystal Display Device>

A liquid crystal display device of the present invention includes the polarizing plate of the present invention, it is preferable that the liquid crystal display device includes a liquid crystal cell, and the polarizing plate of the present invention which is arrange on at least one side of the liquid crystal cell, and it is more preferable that the polarizing plate protective film of the present invention included in the polarizing plate described above is arranged to be an outermost layer.

EXAMPLES

Hereinafter, the present invention will be specifically described on the basis of examples. Materials, reagents, substance quantities and ratios thereof, operations, and the like described in the following examples are able to be suitably changed insofar as the change is not departed from the gist of the present invention. Accordingly, the scope of the present invention is not limited to the following examples.

Synthesis Example 1: Synthesis of A-19

50.0 g of o-cresol, 1.2 g of n-dodecyl mercaptan, and 1.0 g of water were put into 1 L of a three-neck flask including a thermometer, a stirring blade, a dropping funnel, and a reflux cooling pipe, nitrogen substitution was performed in a system, and then, hydrogen chloride gas was blown into the system until the system was saturated at 40° C. A mixed liquid of 35.5 g of o-cresol and 23.7 g of 9-fluorenone was gradually dropped while maintaining the temperature in the system to be 40° C. to 45° C. After the dropping ended, a reaction was further performed at 45° C. for 4 hours. After the reaction ended, 28 g of an aqueous solution of sodium hydroxide of 12% was added, neutralization was performed, 50 g of acetone was added, and crystals were dissolved. After that, cooling was performed to a room temperature, and the educed crystals were filtered.

The obtained crude crystals were dissolved in a large amount of acetone and were recrystallized, and thus, a target compound A-19 was obtained (39 g, white crystals).

Synthesis Example 2: Synthesis of A-18

In Synthesis Example 1, a target compound A-18 was obtained by the same method as that in Synthesis Example 1 except that the o-cresol was changed to phenol (40 g, white crystals).

Synthesis Example 3: Synthesis of A-7

In Synthesis Example 1, a target compound A-7 was obtained by the same method as that in Synthesis Example 1 except that the o-cresol was changed to 2,6-dimethyl phenol, and the 9-fluorenone was changed to 2-fluoro-9-fluorenone (40 g, white crystals).

Synthesis Example 4: Synthesis of A-10

In Synthesis Example 1, a target compound A-10 was obtained by the same method as that in Synthesis Example 1 except that the o-cresol was changed to 2-tert-butyl phenol (46 g, white crystals).

Synthesis Example 5: Synthesis of A-16

In Synthesis Example 1, a target compound A-16 was obtained by the same method as that in Synthesis Example 1 except that the o-cresol was changed to phenol, and the 9-fluorenone was changed to 11H-benzo[b]fluoren-11-one, (42 g, yellow-white crystals).

Example 1

[Preparation of Film]
(Dissolving Step: Preparation of (Meth)Acrylic Resin Composition)

Compositions described below were put into a mixing tank and were stirred while being heated, and each component was dissolved, and thus, a (meth)acrylic resin composition was prepared.

(Composition of (Meth)Acrylic Resin Composition)
Resin C 100 parts by mass
Additive A-7 10 parts by mass
Additive B-21 0.5 parts by mass
Dichloromethane 534 parts by mass
Methanol 46 parts by mass <Film Formation of Film>
(Casting Step)

The prepared (meth)acrylic resin composition was homogeneously cast onto a stainless steel endless band (a casting support) having a width of 2,000 mm from a casting die by using a film manufacturing line as illustrated in FIG. 1, and thus, a casting film was formed.

(Peeling Step)

The casting film was peeled out from the casting support as a film at a time point where the amount of residual solvent in the (meth)acrylic resin composition became 20 mass %.

The casting film was transported by a tenter without being actively stretched, and was dried in a drying zone at 140° C.

A film having a thickness of 40 µm was prepared through the steps described above. A single layer film of the film obtained as described above was set to a polarizing plate protective film of Example 1.

Polarizing plate protective films of Examples 2 to 14, and Comparative Examples 1 to 5 were obtained by the same method as that in Example 1 except that an (meth)acrylic resin and an additive in the (meth)acrylic resin composition, and the added amount of the additive were changed as shown in Table 1. Furthermore, in all of the examples and the comparative examples, the content of the "resin" is 100 parts by mass.

The haze, the coloration, Tg, and the moisture permeability of the obtained polarizing plate protective film were measured by the following method, and the obtained results were shown in Table 1 described below.

[Evaluation of Polarizing Plate Protective Film]
(Haze)

In the measurement of the haze, a film sample cut out from the polarizing plate protective film to have a size of 40 mm×80 mm was measured at a temperature of 25° C. and relative humidity of 60% by using a hazemeter "HGM-2DP" {manufactured by Suga Test Instruments Co., Ltd.} according to JIS K-6714.

A: The haze is less than or equal to 1.0%.
B: The haze is greater than 1.0%.
C: The film is whitened, and thus, the haze is not able to be measured.

(Coloration)

The coloration was sensory-evaluated on the basis of the following criteria by visually observing the polarizing plate protective film after film formation.

A: The polarizing plate protective film is colorless and transparent in visual observation.
B: The polarizing plate protective film slightly exhibits a yellow color in visual observation.
C: The polarizing plate protective film obviously exhibits a yellow color in visual observation.

(Tg)

In the measurement of Tg, a film sample cut out from the polarizing plate protective film to have a size of 5 mm×25 mm was measured by using a dynamic viscoelasticity measurement device Rheogel-E4000HP (manufactured by UBM Co., Ltd.), and Tg was obtained by being calculated from an E' shoulder.

(Moisture Permeability)

As described above, the moisture permeability of the film measured in conditions of a temperature of 40° C. and relative humidity of 90% was calculated on the basis of a method defined in JIS Z-0208(1976) (moisture permeability in terms of 40 μm).

Mw=100,000, Compositional Ratio of Structural Unit MMA/MA=95/5 (Mass Ratio)

Resin B—DIANAL BR85, manufactured by Mitsubishi Rayon Co., Ltd., Weight-Average Molecular Weight Mw=400,000, Structural Unit MMA=100 (mass %)

Resin C—DIANAL BR88, manufactured by Mitsubishi Rayon Co., Ltd., Weight-Average Molecular Weight Mw=1,000,000, Structural Unit MMA=100 (mass %)

In addition, "TAC" indicates triacetyl cellulose (LT-35, manufactured by Daicel Corporation), and "PC" indicates polycarbonate (PANLITE L-1250Y, manufactured by TEIJIN LIMITED.).

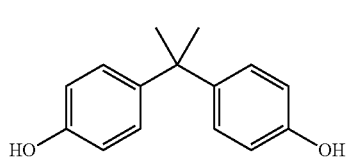

H-1

From Table 1 described above, it was found that in the polarizing plate protective film of each of the examples, the haze value was low and the coloration was suppressed without considerably decreasing Tg, and the moisture permeability was excellent.

INDUSTRIAL APPLICABILITY

According to the present invention, it is possible to provide a (meth)acrylic resin composition from which a film having high Tg, excellent heat resistance, low haze, reduced coloration, and low moisture permeability is able to be manufactured. In addition, according to the present invention, it is possible to provide a film formed by using the (meth)acrylic resin composition, and a polarizing plate and a liquid crystal display device including the film.

TABLE 1

| | Compound of General Formula (1) | | Compound Preventing Compound of General Formula (1) from Being Oxidized | | Film Evaluation | | | |
|---|---|---|---|---|---|---|---|---|
| | Number | Added Amount [Parts by Mass] | Number | Added Amount [Parts by Mass] | Resin Number | Haze | Coloration | Tg [° C.] | Moisture Permeability [g/m²/day] |
| Example 1 | A-7 | 10 | B-21 | 0.5 | C | A | B | 110 | 55 |
| Example 2 | A-10 | 10 | B-18 | 0.5 | C | A | B | 110 | 52 |
| Example 3 | A-10 | 20 | B-22 | 1 | C | A | B | 105 | 48 |
| Example 4 | A-16 | 10 | B-23 | 0.5 | C | A | B | 110 | 50 |
| Example 5 | A-19 | 10 | B-24 | 0.5 | A | A | B | 100 | 49 |
| Example 6 | A-19 | 10 | B-21 | 0.5 | B | A | B | 105 | 49 |
| Example 7 | A-19 | 10 | B-21 | 0.5 | C | A | B | 110 | 48 |
| Example 8 | A-19 | 20 | B-21 | 1 | C | A | B | 110 | 41 |
| Example 9 | A-19 | 20 | B-7 | 1 | C | A | A | 110 | 41 |
| Example 10 | A-19 | 20 | B-15 | 1 | C | A | A | 110 | 41 |
| Example 11 | A-18 | 20 | B-13 | 1 | C | A | A | 110 | 42 |
| Example 12 | A-19 | 20 | B-13 | 1 | C | A | A | 110 | 41 |
| Example 13 | A-19 | 30 | B-7 | 1 | C | A | B | 110 | 32 |
| Example 14 | A-19 | 30 | B-13 | 1 | C | A | A | 110 | 32 |
| Comparative Example 1 | A-18 | 20 | None | None | TAC | B | C | 100 | 590 |
| Comparative Example 2 | A-18 | 20 | None | None | PC | B | C | 120 | 80 |
| Comparative Example 3 | A-18 | 20 | None | None | C | A | C | 110 | 42 |
| Comparative Example 4 | H-1 | 10 | None | None | C | A | C | 95 | 100 |
| Comparative Example 5 | None | None | None | None | C | A | A | 120 | 75 |

In Table 1 described above, resins A to C are as follows. MMA indicates a structural unit derived from methyl methacrylate, and MA indicates a structural unit derived from methyl acrylate.

Resin A—DELPET 80N, manufactured by Asahi Kasei Corporation, Weight-Average Molecular Weight The present invention has been described in detail with reference to specific embodiments, but it is obvious to a person skilled in the art that various changes or corrections are able to be performed without departing from the scope and the range of the present invention.

This application is based on Japanese Patent Application (JP2014-070533), filed on Mar. 28, 2014, and the contents are incorporated herein as reference.

EXPLANATION OF REFERENCES

20: film manufacturing line
21: stock tank
22: dope composition
30: filtration device
31: casting die
32, 33: rotating roller
34: metal support
35: tenter type drier
40: selvage cutting device
41: drying chamber
42: cooling chamber
43: winding chamber
60: motor
61: stirrer
63: heat medium circulation device
64: casting chamber
65: temperature adjustment equipment
66: condenser
67: collecting device
68: decompression chamber
69: casting film
70, 71, 72, 73: blowing port
74: wet film
80: crossover portion
81: blowing machine
82: film
90: crusher
91: roller
92: adsorption collecting device
93: forced static elimination device (static elimination bar)
94: knurling applying roller
95: winding roller
96: press roller

What is claimed is:

1. A (meth)acrylic resin composition, containing:
a (meth)acrylic resin;
a compound denoted by General Formula (1); and
a compound preventing the compound denoted by General Formula (1) described below from being oxidized:

General Formula (1)

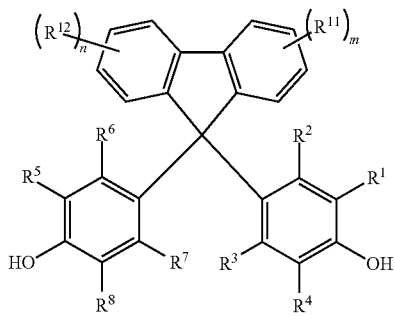

wherein $R^1$ to $R^8$ each independently represent a hydrogen atom, a halogen atom, a hydroxyl group, or a hydrocarbon group having 1 to 6 carbon atoms, $R^{11}$ and $R^{12}$ each independently represent a hydrogen atom, a halogen atom, or a hydrocarbon group having 1 to 12 carbon atoms, m and n each independently represent an integer of 0 to 4, and in a case in which m and n represent an integer of greater than or equal to 2, a plurality of $R^{11}$'s and $R^{12}$'s may be identical to each other or different from each other, and at least two $R^{11}$'s, at least two $R^{12}$'s, or $R^{11}$ and $R^{12}$ may form a ring by being linked to each other.

2. The (meth)acrylic resin composition according to claim 1,
wherein in General Formula (1), $R^2$, $R^3$, $R^4$, $R^6$, $R^7$, and $R^8$ represent a hydrogen atom.

3. The (meth)acrylic resin composition according to claim 1,
wherein in General Formula (1), $R^1$ and $R^5$ each independently represent a hydrogen atom or a methyl group.

4. The (meth)acrylic resin composition according to claim 1,
wherein in General Formula (1), m and n represent 0.

5. The (meth)acrylic resin composition according to claim 1,
wherein the compound preventing the compound denoted by General Formula (1) from being oxidized is a phenol-based antioxidant, a sulfur-based antioxidant, or an amide-based antioxidant.

6. The (meth)acrylic resin composition according to claim 1,
wherein a weight-average molecular weight of the (meth)acrylic resin is 80,000 to 2,500,000.

7. The (meth)acrylic resin composition according to claim 6,
wherein the weight-average molecular weight of the (meth)acrylic resin is 250,000 to 2,000,000.

8. The (meth)acrylic resin composition according to claim 1,
wherein the (meth)acrylic resin is a (meth)acrylic resin in which a content ratio of a structural unit derived from methyl methacrylate is greater than or equal to 95 mass %, and a content ratio of a structural unit derived from alkyl (meth)acrylate other than the methyl methacrylate is less than 5 mass %.

9. A film obtained by performing film formation with respect to the (meth)acrylic resin composition according to claim 1.

10. A polarizing plate protective film, comprising:
the film according to claim 9.

11. A polarizing plate, comprising:
the polarizing plate protective film according to claim 10.

12. A liquid crystal display device, comprising:
the polarizing plate according to claim 11.

* * * * *